Figures 1A, 1B:
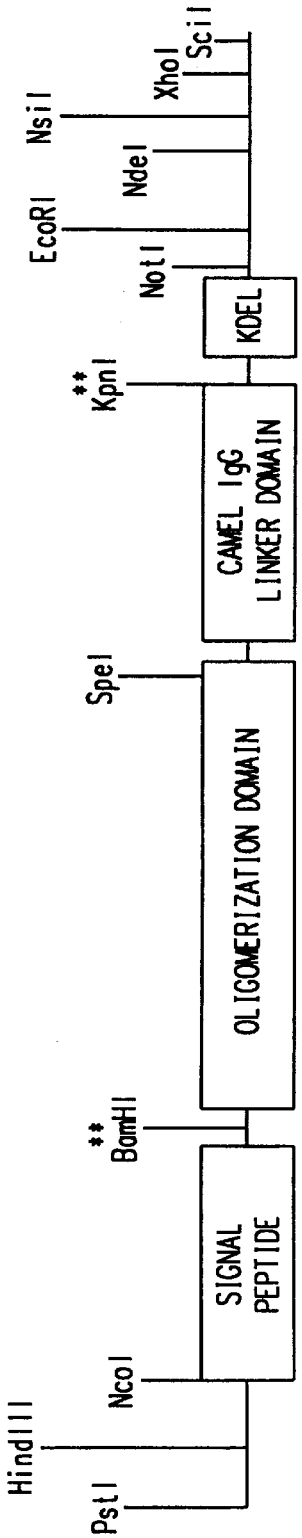

United States Patent [19]
Rothman et al.

[11] Patent Number: 6,160,088
[45] Date of Patent: Dec. 12, 2000

[54] KDEL RECEPTOR INHIBITORS

[75] Inventors: James E. Rothman, New York; Mark Mayhew, Tarrytown; Mee H. Hoe, Irvington, all of N.Y.

[73] Assignee: Sloan-Kettering Institute For Cancer, New York, N.Y.

[21] Appl. No.: 09/124,671

[22] Filed: Jul. 29, 1998

[51] Int. Cl.[7] ............................. A61K 38/00; C07K 1/00
[52] U.S. Cl. ............................................ 530/324; 530/350
[58] Field of Search ..................................... 530/324, 350

[56] References Cited

PUBLICATIONS

Arap et al., 1998, Science 279:377–380.
Kim et al., 1998, Proc. Natl. Acad. Sci. U.S.A. 95:2997–3002.
Lammert et al., 1997, Eur. J. Immunol. 27:1685–1690.
Terskikh et al., 1997, Proc. Natl. Acad. Sci. U.S.A. 94:1663–1668.
Zufferey et al., 1997, Nature Biotechnology 15:871–875.
Malashkevich et al., 1996, Science 274:761–765.
Miesenböck and Rothman, 1995, J. Cell. Biol. 129:309–319.
Efimov et al., 1994, FEBS Letters 341:54–58.
Townsley et al., 1993, EMBO J. 12:2821–2829.
Wilson et al., 1993, J. Biol. Chem. 268:7465–7468.
Bornstein, 1992, FASEB J. 6:3290–3299.
Lewis and Pelham, 1992, J. Mol. Biol. 226:913–916.
Lewis and Pelham, 1992, Cell 68:353–364.
Semenza and Pelham, 1992, J. Mol. Biol. 224:1–5.
Flynn et al., 1991, Nature 353:726–730.
Flynn et al., 1989, Science 245:385–390.
Pelham, 1988, EMBO J. 7:913–918.
Munro and Pelham, 1987, Cell 48:899–907.
Wearsch, P. et al., Biochem., vol. 35, pp. 16760–16769, 1996.

Primary Examiner—Ponnathapu Achutamurthy
Assistant Examiner—Peter P. Tung

[57] ABSTRACT

The present invention relates to inhibitors of the KDEL receptor and therapeutic uses therefor. Certain proteins are functionally retained in the cellular endoplasmic reticulum via an interaction between a KDEL sequence and its receptor. According to the invention, blocking this interaction with a KDEL receptor inhibitor promotes the secretion of such proteins. In specific embodiments of the invention, KDEL receptor inhibitors may be used to promote the secretion of heat shock proteins, thereby rendering the secreted heat shock proteins more accessible to the immune system and improving the immune response to heat shock protein-associated antigens.

13 Claims, 30 Drawing Sheets

M G K F T V V A A A L L L L G A V R A E – G S S –
                    ↑
            SIGNAL CLEAVAGE SITE

L G G D L A – P Q M L R E L Q E T N A A L Q D V R E L L R Q Q V K E I T F L K N T V M E C D A C G – M Q P A R T P G T S –

P Q P Q P K P Q P Q P K P Q P Q P K P E P E – G T G S S E – K D E L

M G K F T V V A A A L L L L G A V R A E – G S S –

L G G D C C – G E Q T K A L V T Q L T L F N Q I L V E L R D D I R D Q V K E M S L I R N T I M E C C Q V C G –

P Q P Q P K P Q P Q P Q P Q P K P Q P K P E P E – G T G S S E – K D E L

SIGNAL CLEAVAGE SITE

M G K F T V V A A A L L L L L G A V R A E – G S S –

L G G D C C – G D V S R Q L I G Q I T Q M N Q M L G E L R D V M R Q Q V K E T M F L R N T I A E C Q A C G –

P Q P Q P K P Q P Q P Q P K P Q P K P E P E – G T G S S E – K D E L

M R Y M I L G L L A L A A V C S A A K K - G S S -

L G G D C C - S D L G P Q M L R E L Q E T N A A L Q D V R D W L R Q Q V R E I T F L K N T V M E C D A C G -

P Q P Q P K P Q P Q P K P Q P Q P K P E P E - G T G S S E - K D E L

M R Y M I L G L L A L A A V C S A A K K — G S S —

↑ SIGNAL CLEAVAGE SITE

L G G D C C — Q K L Q N L F I N F C L I L I C L L L I C I I V M L L —

P Q P Q P K P Q P Q P Q P K P Q P K P E P E — G T G S S E — K D E L

• RESIDUES CRITICAL FOR PENTAMER FORMATION

KDEL RECEPTOR INHIBITORS

2. BACKGROUND OF THE INVENTION

A living cell is a complex assembly of molecular elements; to function properly, its constituent molecules must form associations and operate in an organized manner. Certain components bind together to form molecular superstructures, including organelles which compartmentalize cellular activities and filaments which impart order and control motility. Other components exist in soluble form, and may move freely throughout the cell or, alternatively, within a subcellular compartment.

Cells are also equipped with elements that synthesize, process, and secrete a designated subset of proteins. This so-called secretory pathway includes membrane associated structures, such as the endoplasmic reticulum and Golgi apparatus, as well as a number of resident soluble molecules which participate in the processing of secreted proteins. Proteins which are to be secreted pass through the Golgi apparatus, where they are packaged for export from the cell. Accompanying them, by virtue of the continual vesicular transport of membrane and endoplasmic reticulum luminal contents, are soluble proteins properly residing in the endoplasmic reticulum.

To avoid continuously losing and needing to resynthesize these resident proteins, the cell uses a membrane-bound receptor localized in or near the Golgi apparatus for their retrieval (Lewis and Pelham, 1992, Cell 68:353–364). The receptor binds to a specific carboxy-terminal amino acid sequence which serves as a marker of what proteins are to be returned to the endoplasmic reticulum; this sequence is generally lysine-aspartic acid-glutamic acid-leucine (Lys-Asp-Glu-Leu in the three-letter amino acid code, KDEL in the single-letter code, referred to herein as "KDEL"), so that the receptor is generally referred to as the KDEL (SEQ ID NO:37) receptor (Munro and Pelham, 1987, Cell 48:899–907; Pelham, 1988, EMBO J. 7:913–918). The human KDEL receptor has been characterized as a seven-transmembrane domain protein which is a temporary resident of the Golgi apparatus: upon binding to a KDEL (SEQ ID NO:37)-containing ligand, it moves to the endoplasmic reticulum, where the ligand is released (Townsley et al., 1993, EMBO J. 12:2821–2829).

Among the molecules interacting with the KDEL receptor are certain members of a class of proteins, referred to as "heat shock proteins", which form associations with nascent polypeptides in the endoplasmic reticulum and act as molecular "chaperones", escorting a protein through the assembly process prior to its secretion (Frydman et al., 1994, Nature 370:111–117; Hendrick and Hartl, Annu. Rev. Biochem. 62:349–384; Hartl, 1996, Nature 381:571–580). Heat shock proteins constitute a highly conserved class of proteins selectively expressed in cells under stressful conditions, such as sudden increases in temperature or glucose deprivation. Able to bind to a wide variety of other proteins in their non-native state, heat shock proteins participate in the manufacture of these bound proteins, including their synthesis, folding, assembly, disassembly and translocation (Freeman and Morimoto, 1996, EMBO J. 15:2969–2979; Lindquist and Craig, 1988, Annu. Rev. Genet. 22:631–677; Hendrick and Hartl, 1993, Annu. Rev. Biochem. 62:349–384).

Two heat shock proteins which contain ligand sequences for the KDEL receptor are gp96 and BiP. Found in higher eukaryotes but not in Drosophila or yeast, gp96 appears to have evolved relatively recently, perhaps by a duplication of the gene encoding the cytosolic heat shock protein hsp90, to which it is highly related (Li and Srivastava, 1993, EMBO J. 12:3143–3151; identity between human hsp90 and murine gp96 is about 48 percent; Wiech et al., 1992, Nature 358:169–170; Melnick et al., 1992, J. Biol. Chem. 267:21303–21306; Melnick et al., 1994, Nature 370:373–375; Schaiff et al., 1992, J. Exp. Med. 176:657–666; Ramakrishnan et al., 1995, DNA and Cell Biol. 14:373–384). BiP (also referred to in the literature as grp78) forms a complex with newly synthesized immunoglobulin chains (Bole et al., 1986, J. Cell Biol. 102:1558–1566).

Under certain circumstances, it may be desirable to interfere with the normal control of KDEL (SEQ ID NO:37)-mediated protein redistribution. According to the present invention, a subject may benefit, for example, from the secretion of heat shock proteins which are normally retained in the endoplasmic reticulum but which have beneficial immunogenic effects when released.

Heat shock proteins are believed to play a role in the immune response in several contexts. Inoculation with heat shock protein prepared from tumors of experimental animals has been shown to induce immune responses in a tumor-specific manner; that is to say, heat shock protein gp96 purified from a particular tumor could induce an immune response which would inhibit the growth of cells from the identical tumor of origin, but not other tumors, regardless of relatedness (Srivastava and Maki, 1991, Curr. Topics Microbiol. 167:109–123). High-resolution gel electrophoresis has indicated that tumor-derived gp96 may be heterogeneous at the molecular level; evidence suggests that the source of this heterogeneity may be populations of small peptides adherent to the heat shock protein, which may number in the hundreds (Feldweg and Srivastava, 1995, Int. J. Cancer 63:310–314). Indeed, an antigenic peptide of vesicular stomatitis virus has been shown to associate with gp96 in virus infected cells (Nieland et al., 1996, Proc. Natl. Acad. Sci. U.S.A. 93:6135–6139). It has been suggested that this accumulation of peptides is related to the localization of gp96 in the endoplasmic reticulum, where it may act as a peptide acceptor and accessory to peptide loading of major histocompatability complex class I molecules (Li and Srivastava, 1993, EMBO J. 12:3143–3151; Suto and Srivastava, 1995, Science 269:1585–1588). Recent studies have shown that protein disulfide isomerase ("PDI"), a resident luminal protein of the endoplasmic reticulum having a molecular weight of approximately 60kDa, may also function as a peptide acceptor (Lammert et al., 1997, Eur. J. Immunol. 27:1685–1690).

Further, the use of heat shock proteins as adjuvants to stimulate an immune response has been proposed (see, for example, Edgington, 1995, Bio/Technol. 13:1442–1444; PCT Application International Publication Number WO 94/29459 by the Whitehead Institute for Biomedical Research, Richard Young, inventor, and references infra). One of the best known adjuvants, Freund's complete adjuvant, contains a mixture of heat shock proteins derived from mycobacteria (the genus of the bacterium which causes tuberculosis); Freund's complete adjuvant has been used for years to boost the immune response to non-mycobacterial antigens. A number of references suggest, inter alia, the use of isolated mycobacterial heat shock proteins for a similar purpose, including vaccination against tuberculosis itself (Lukacs et al., 1993, J. Exp. Med. 178:343–348; Lowrie et al., 1994, Vaccine 12:1537–1540; Silva and Lowrie, 1994, Immunology 82:244–248; Lowrie et al., 1995, J. Cell. Biochem. Suppl. 0(19b):220; Retzlaff et al., 1994, Infect.

Immun. 62:5689–5693; PCT Application International Publication No. WO 94/11513 by the Medical Research Council, Colston et al., inventors; PCT Application International Publication No. WO 93/1771 by Biocine Sclavo Spa, Rappuoli et al., inventors).

Increased levels of autologous heat shock proteins may also lead to an improved immune response by virtue of the association of heat shock proteins with endogenous antigenic peptides (International Application No. PCT/US96/13233 by Rothman et al.). Such activity is distinct from the traditionally utilized adjuvant activity of heterologous heat shock proteins.

The present invention is directed toward increasing the secretion of antigenic heat shock protein complexes by inhibiting KDEL receptor-mediated return of such complexes to the endoplasmic reticulum. Analogous methods may be used to increase the secretion of other proteins of interest which normally would tend to be retained via the KDEL receptor.

3. SUMMARY OF THE INVENTION

The present invention relates to inhibitors of the KDEL receptor and therapeutic uses therefor. It is based, at least in part, on the ability of such inhibitors to promote the secretion of proteins which would otherwise tend to be retained in the cell in which they are produced.

In nonlimiting embodiments, the present invention provides for a protein comprising a plurality of amino acid sequences which bind to the KDEL receptor. Such an inhibitory protein, introduced into a cell, would promote the secretion of proteins which would otherwise tend to be functionally retained in the cell via interaction with the KDEL receptor. The secreted proteins may include proteins naturally produced by the cell and/or proteins expressed as a result of the introduction of nucleic acid encoding said proteins into the cell or a progenitor thereof. As specific, nonlimiting examples, the secretion of certain endogenous or exogenously introduced heat shock proteins may be promoted in this manner. Moreover, the KDEL receptor inhibitor protein may be introduced into a cell in conjunction with an antigenic peptide capable of associating with a heat shock protein, and used to promote the secretion of heat shock protein/antigenic peptide complexes.

In further embodiments, the present invention provides for the identification of further compounds, including peptomimetic compounds, which inhibit the association of a KDEL receptor with its protein ligands which may, for example, be prepared by combinatorial chemistry techniques or identified by phage display. Such compounds may be used in methods analogous to those described above to promote the secretion of certain proteins.

4. DESCRIPTION OF THE FIGURES

Figure 1C:
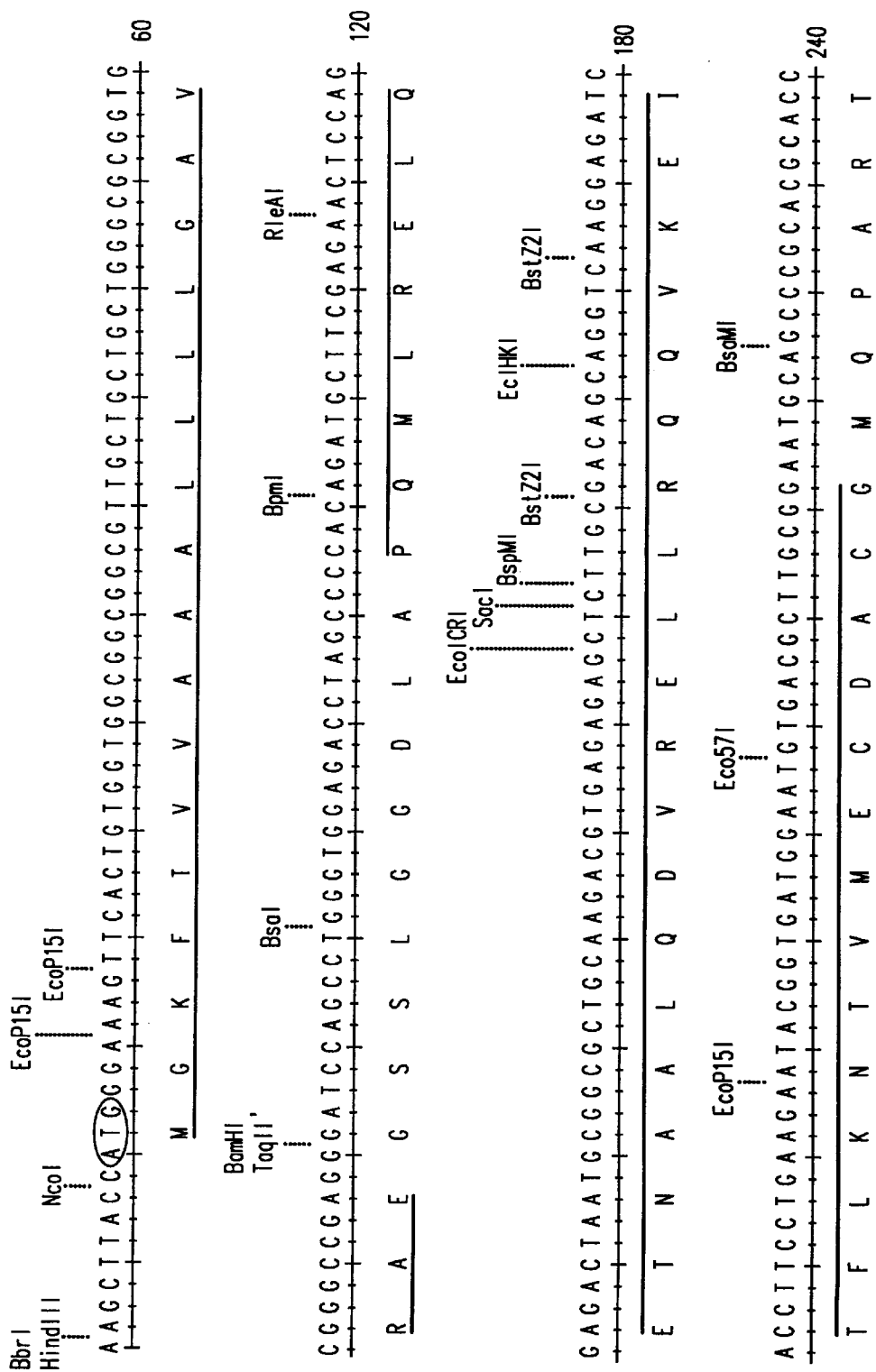
Figure 1D:
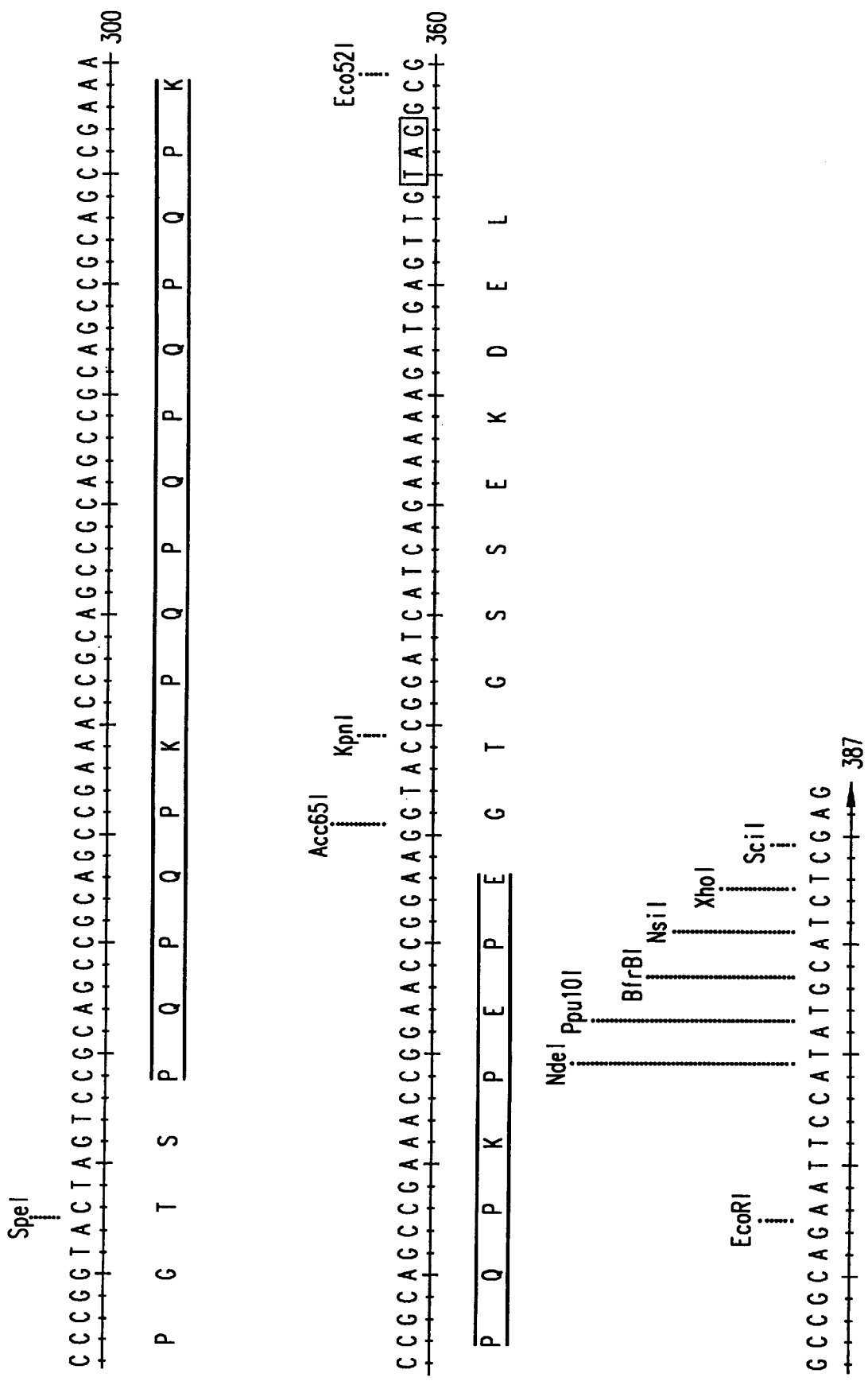
Figure 2A:
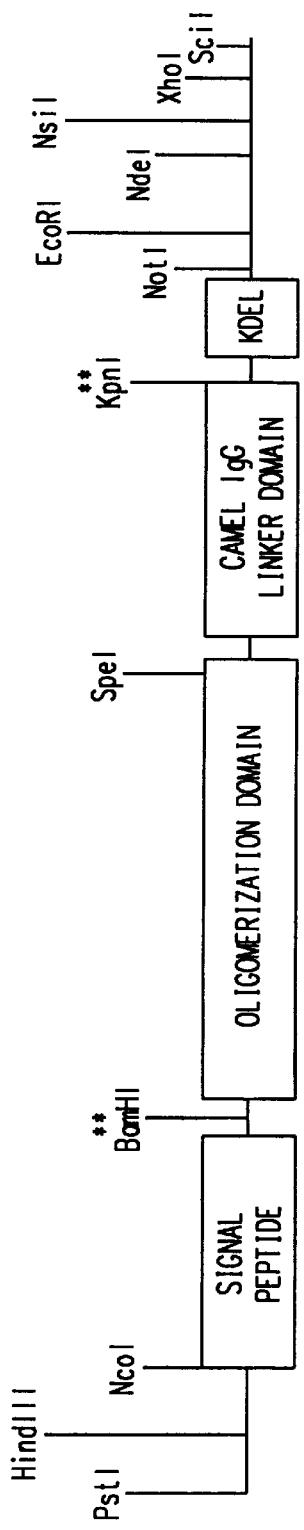
Figure 2B:
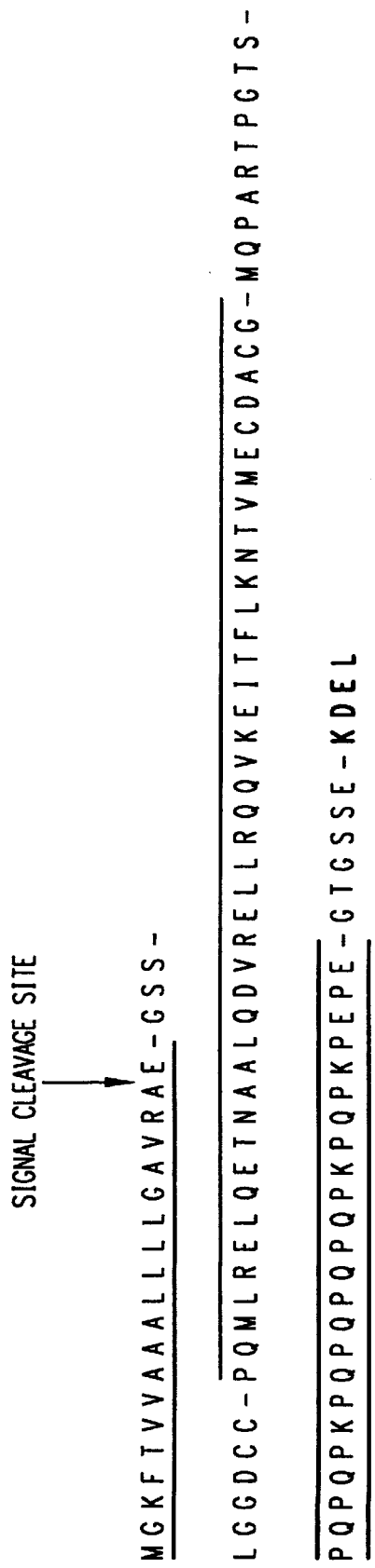
Figure 2C:
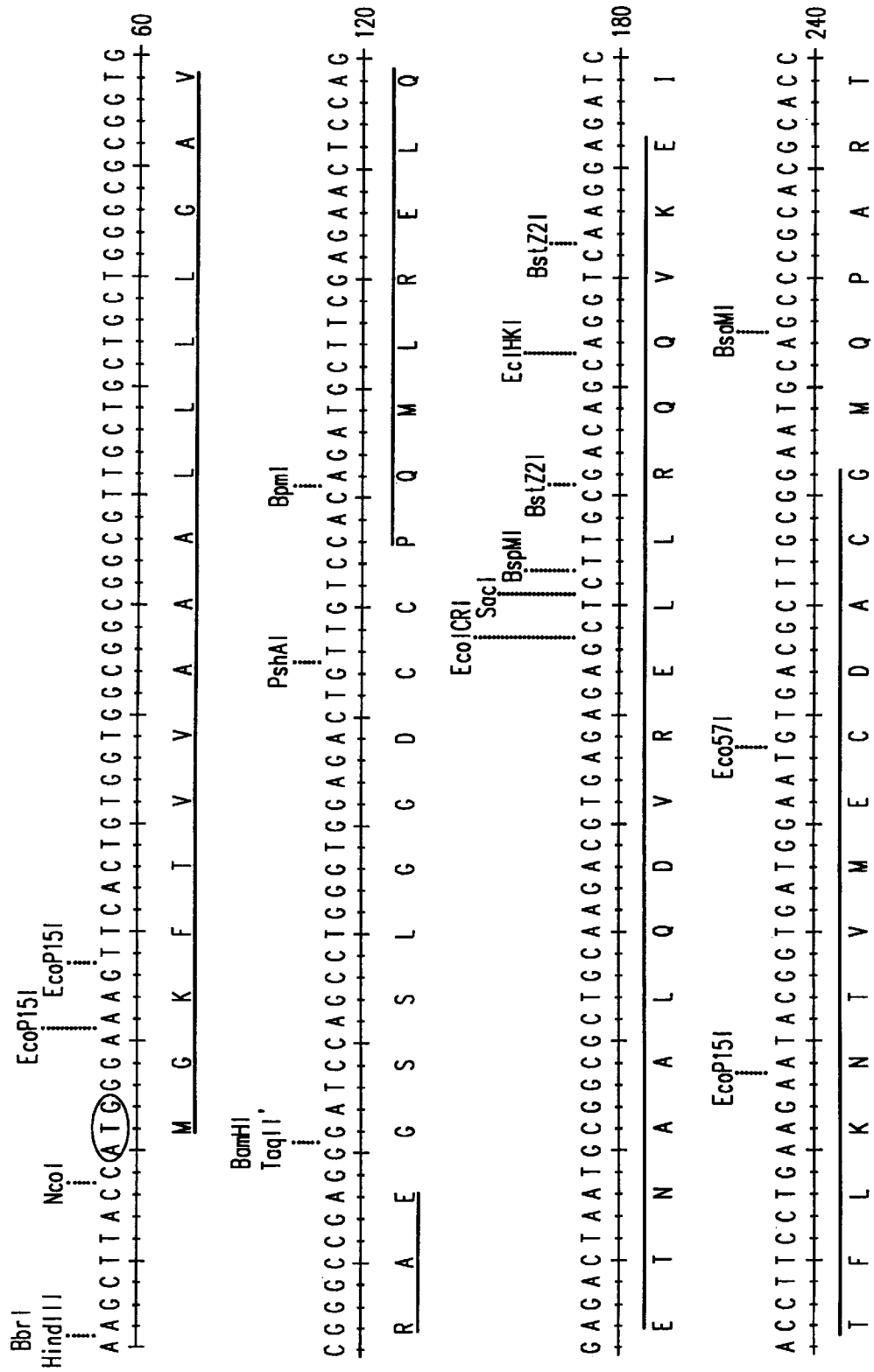
Figure 2D:
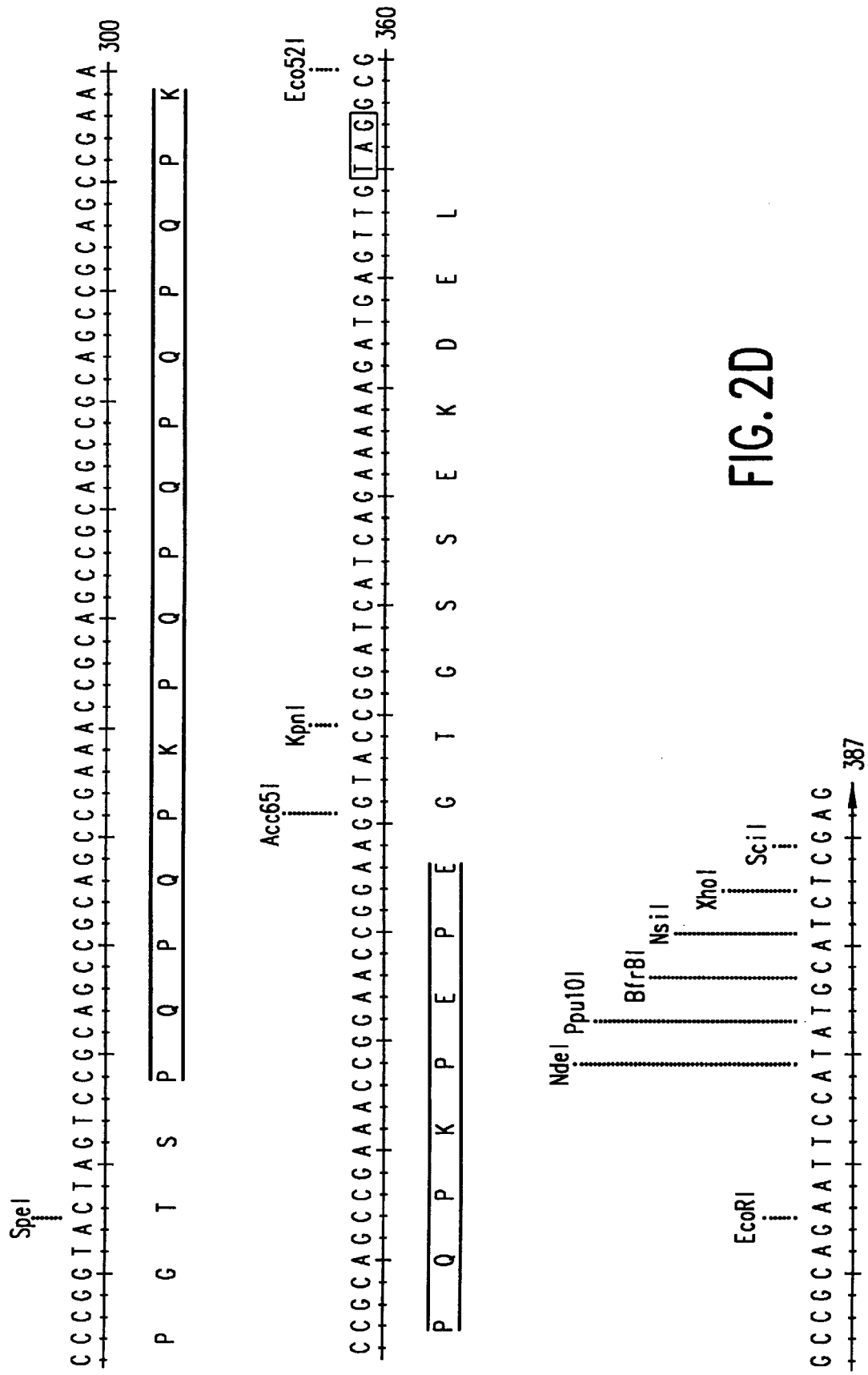
Figure 3A:
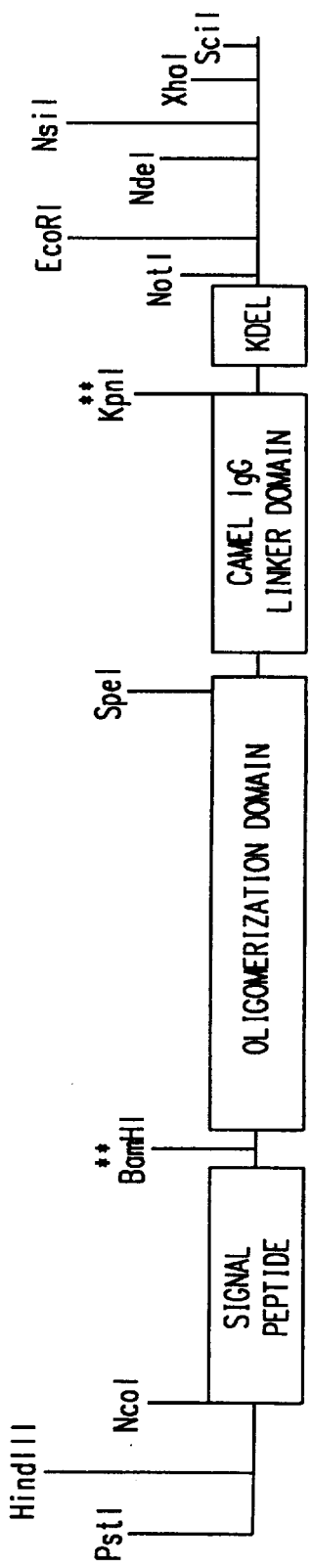
Figure 3B:
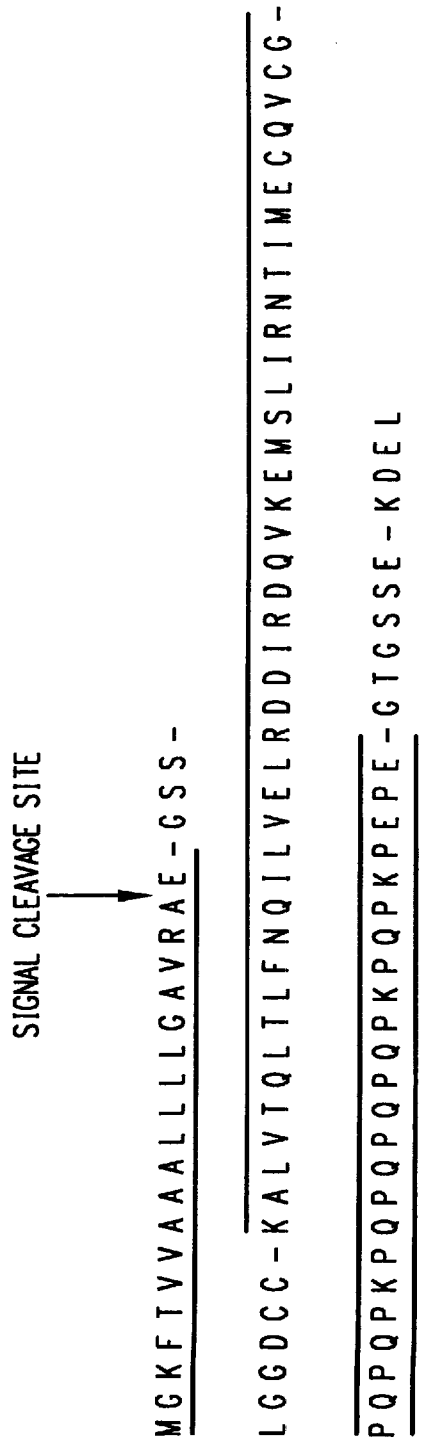
Figure 3C:
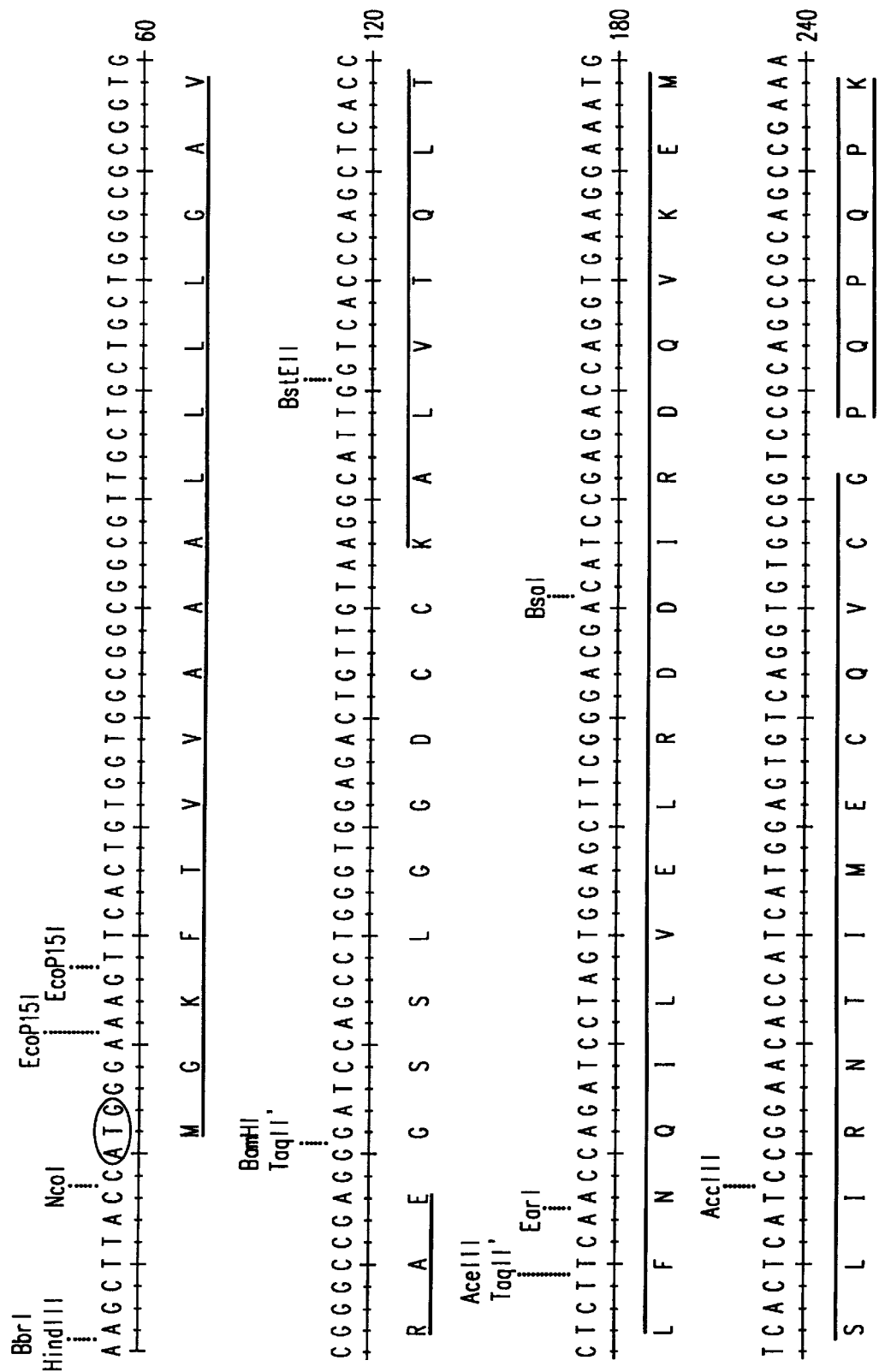
Figure 3D:
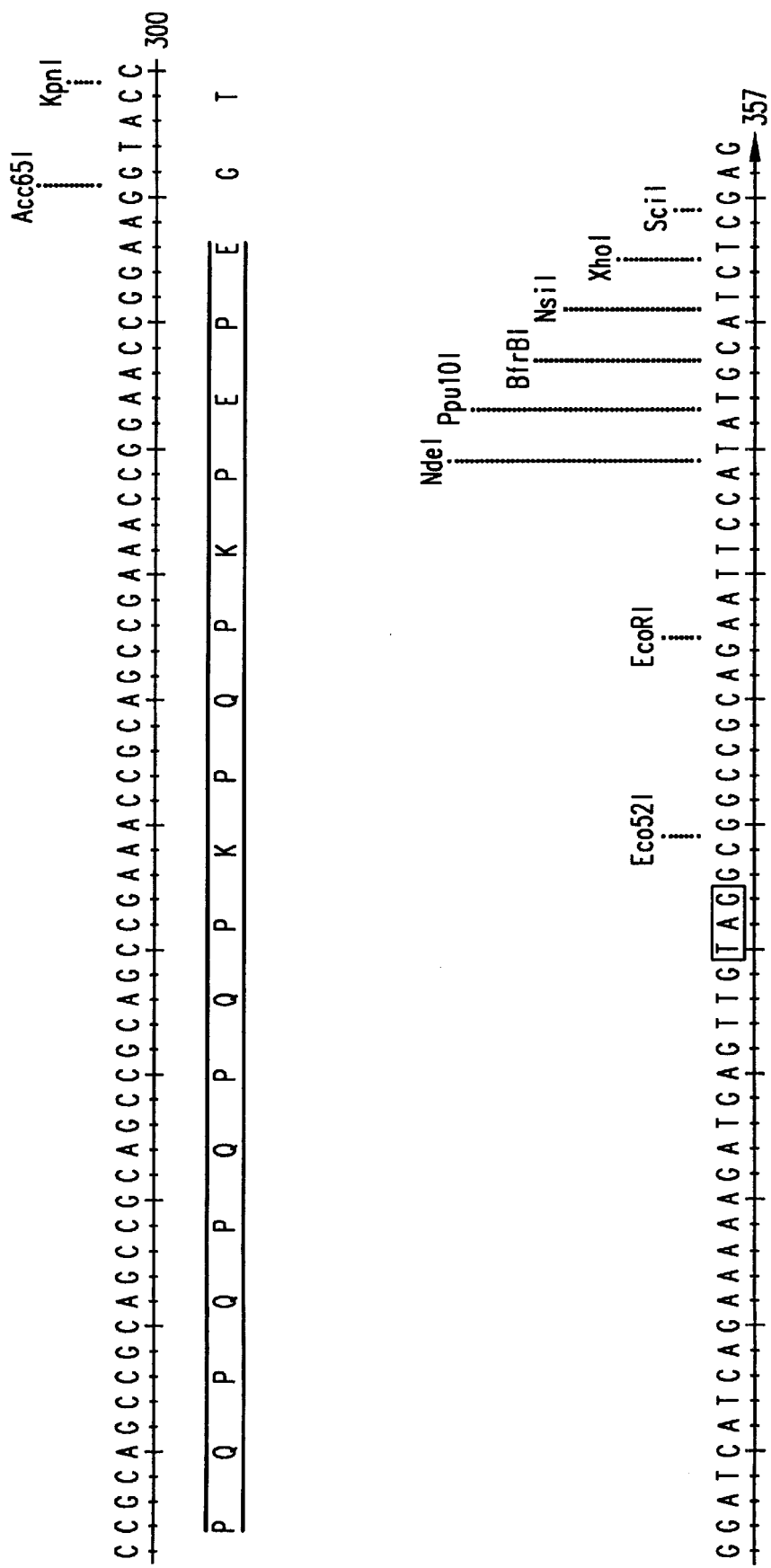
Figure 4A:
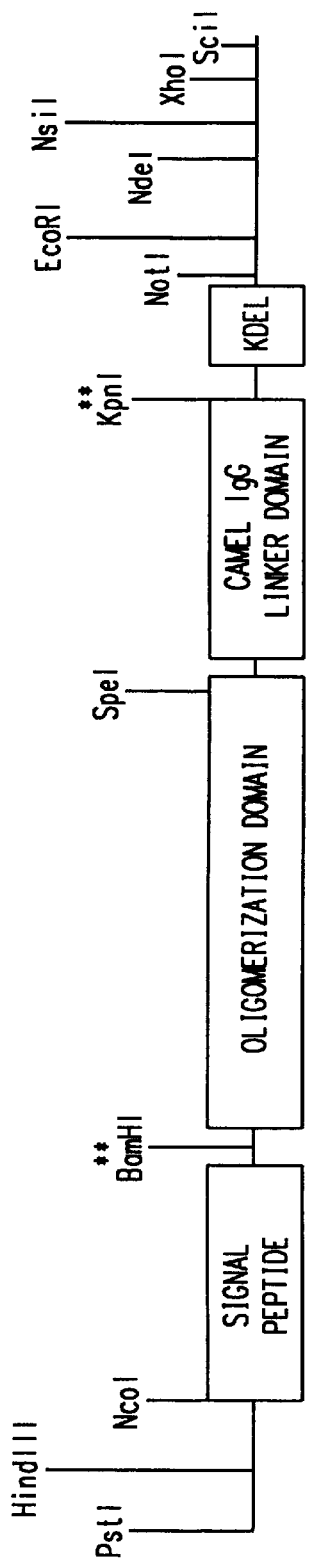
Figure 4B:
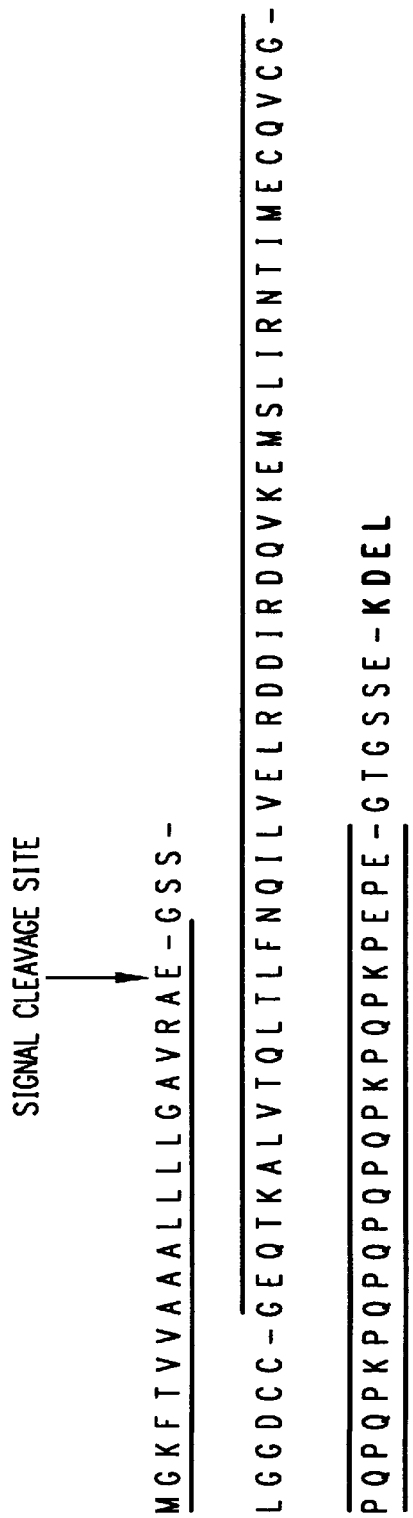
Figure 4C:
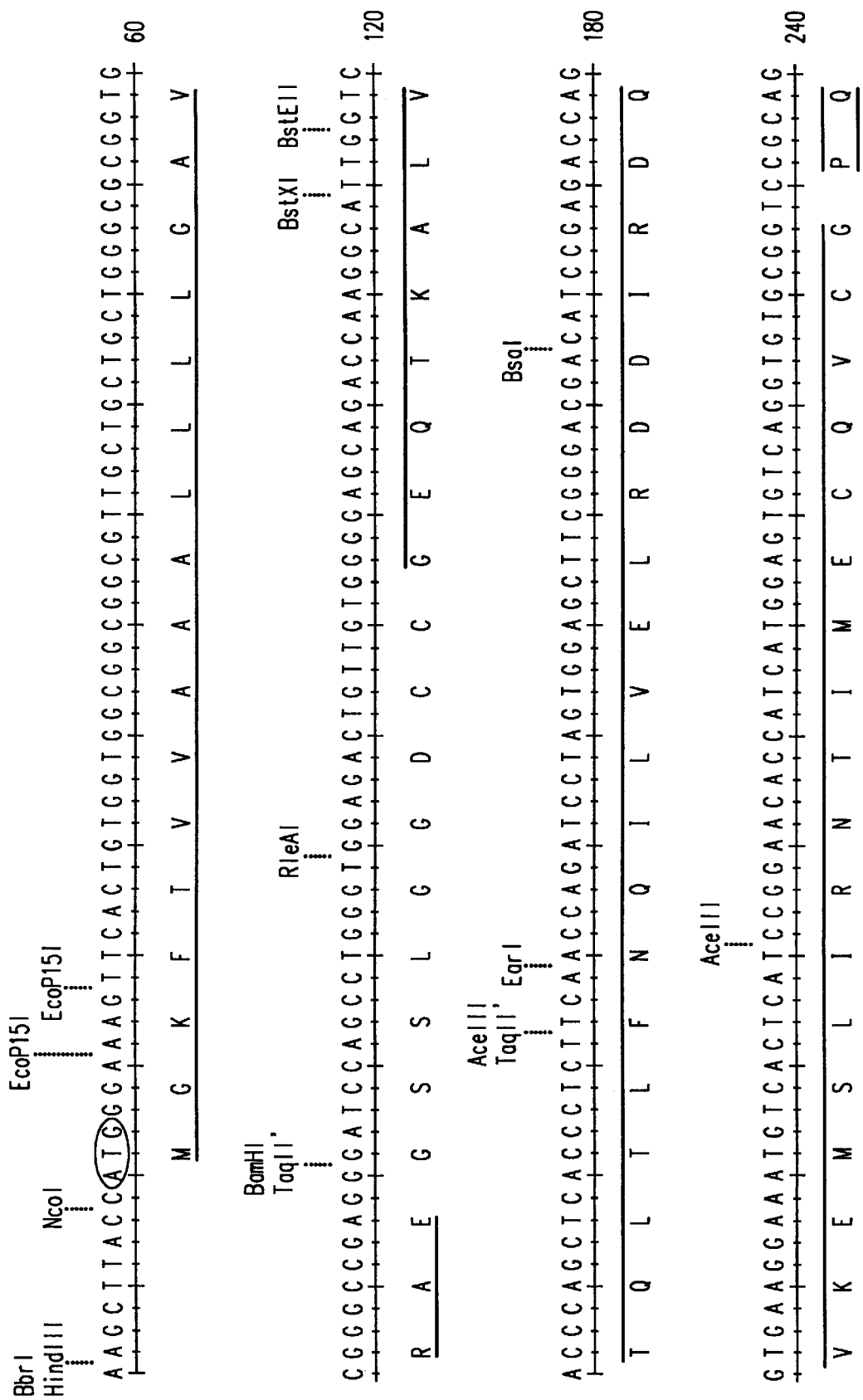
Figure 4D:
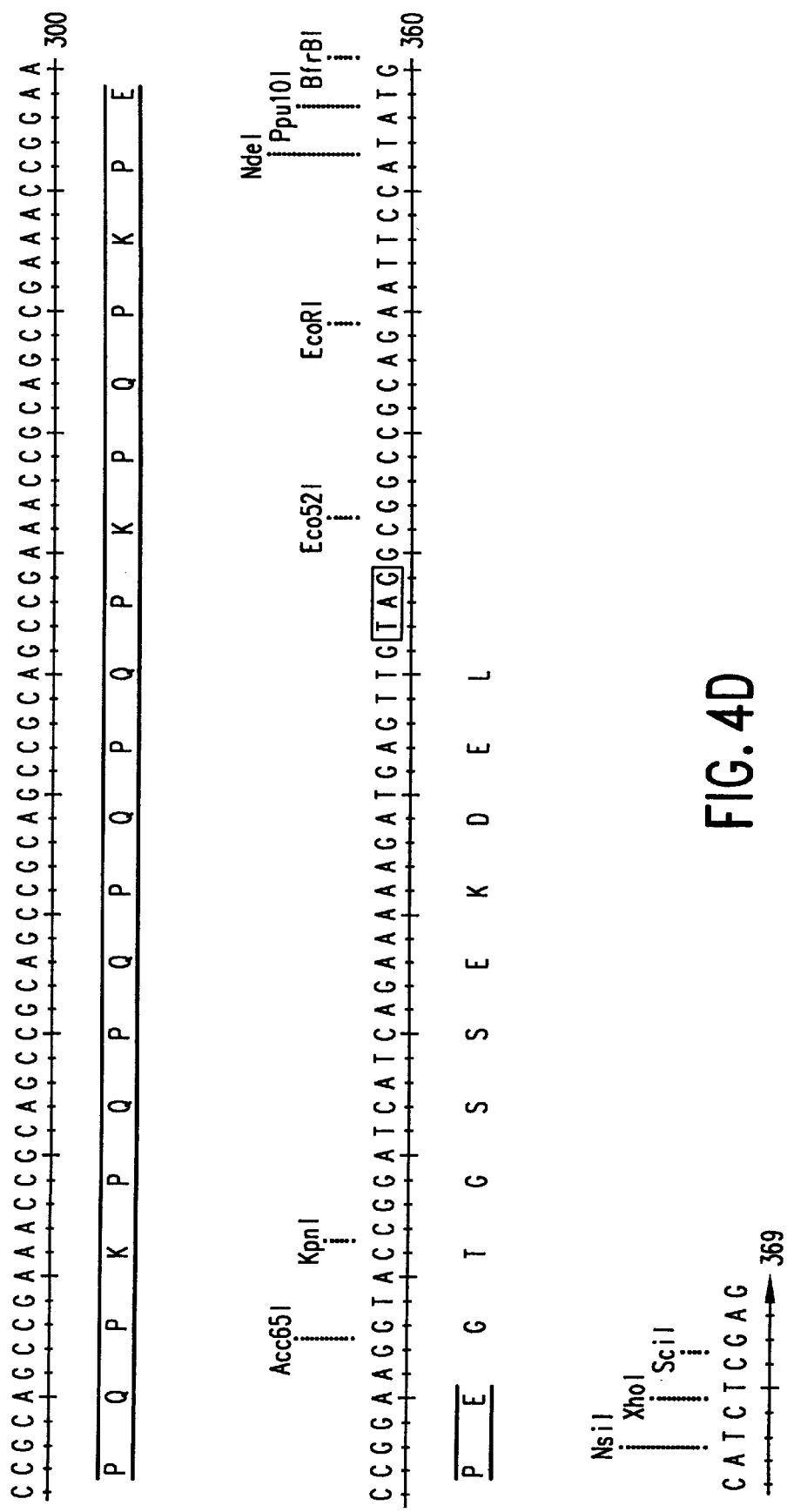
Figure 5A:
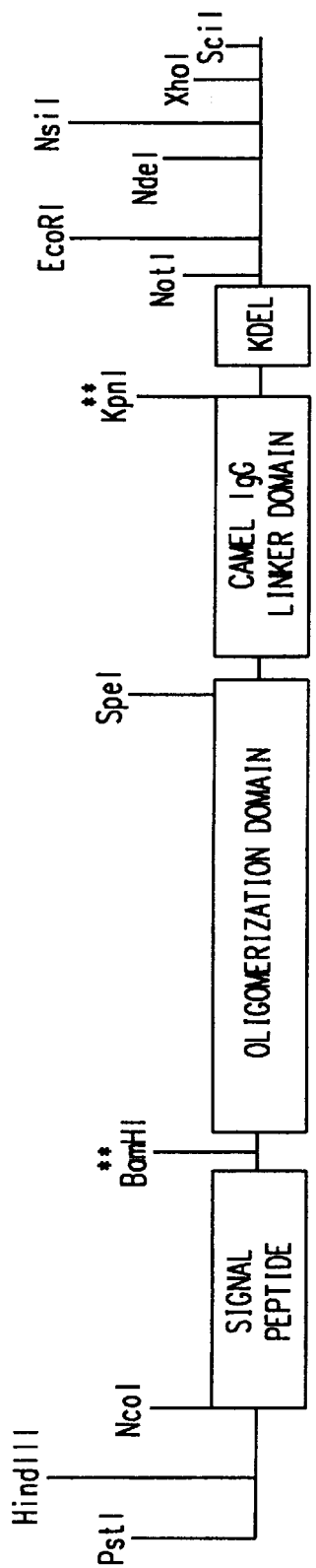
Figure 5B:
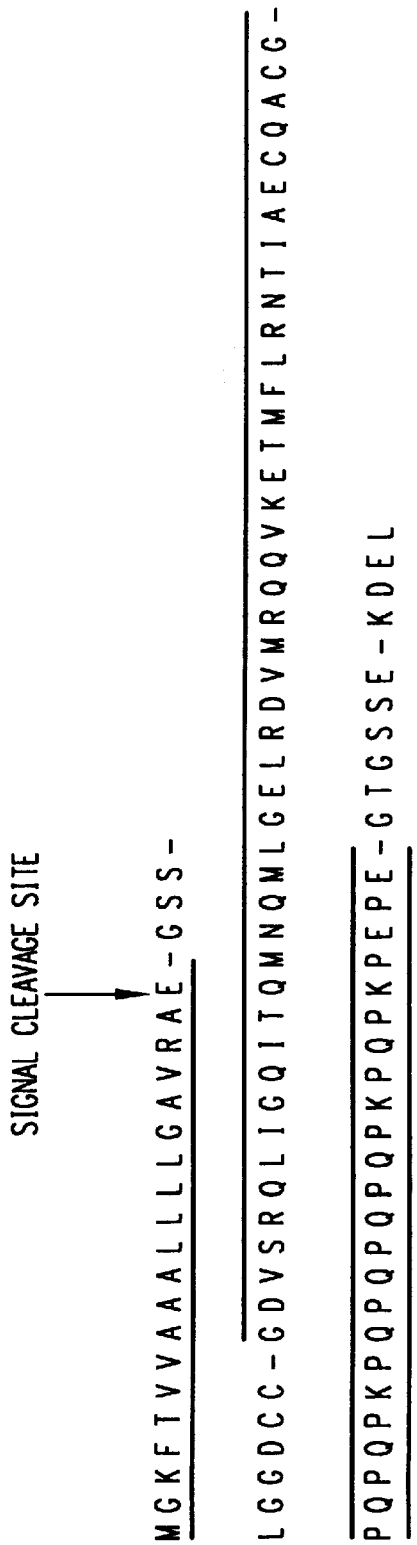
Figure 5C:
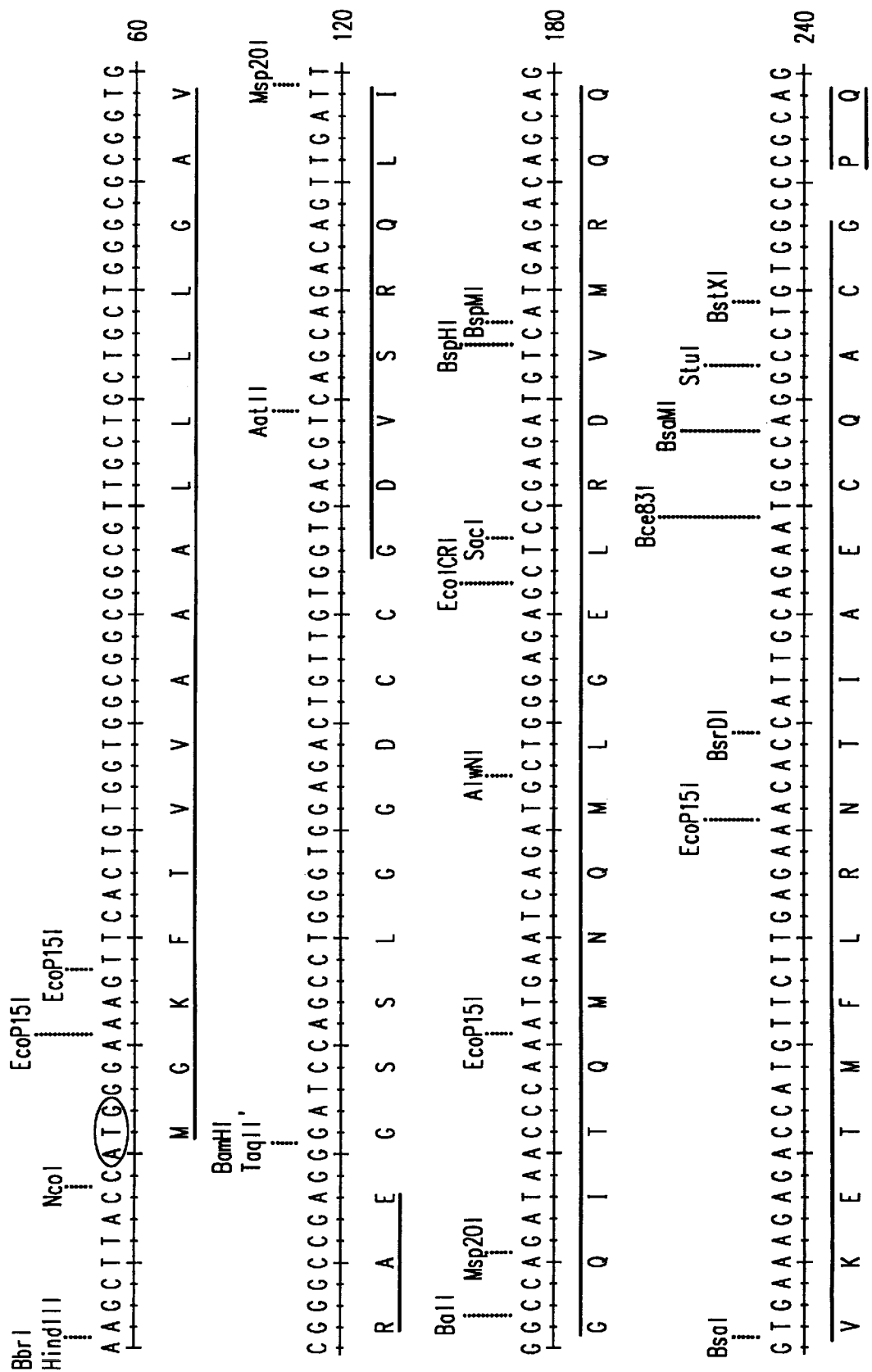
Figure 5D:
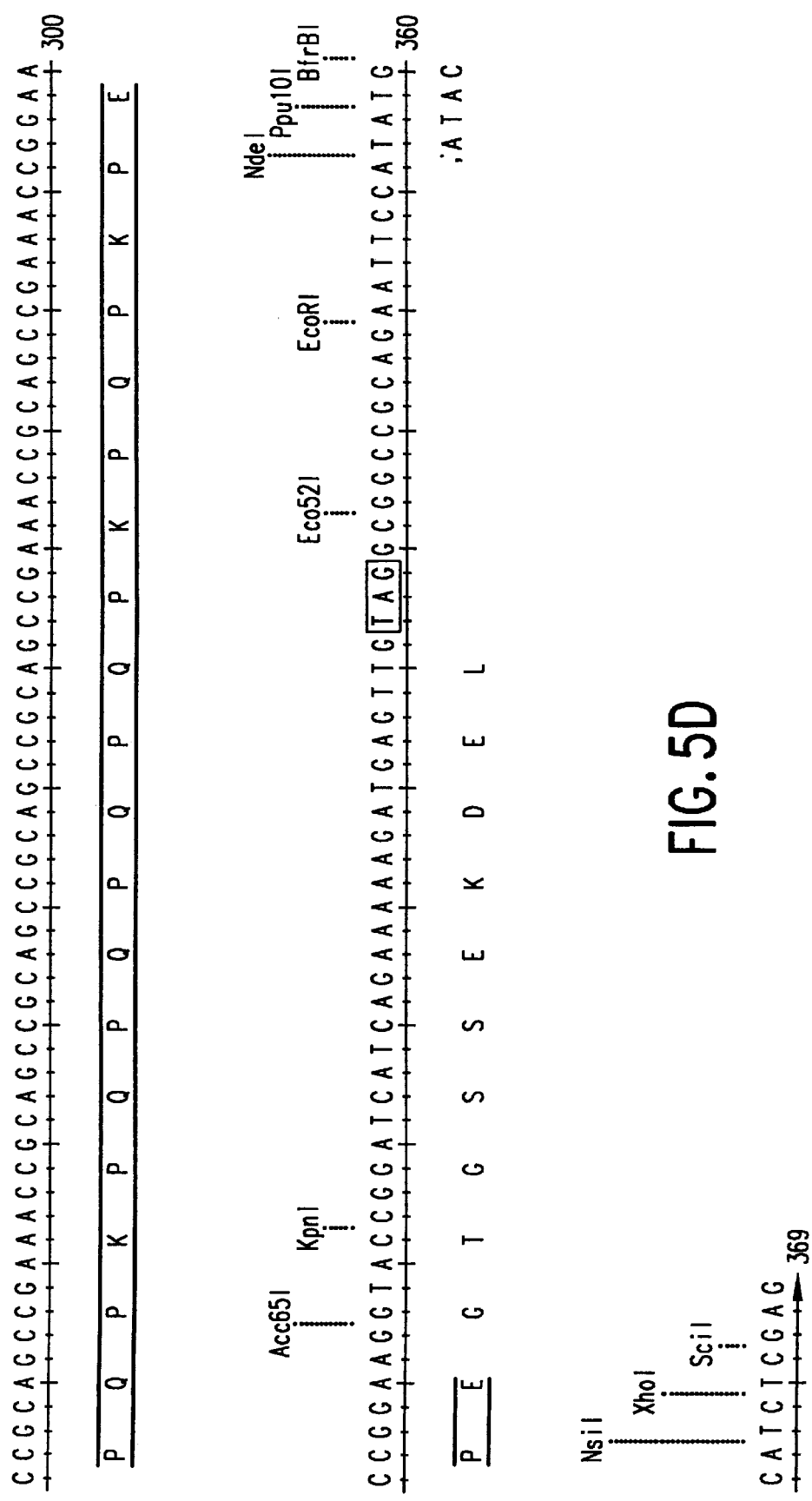
Figure 6A:
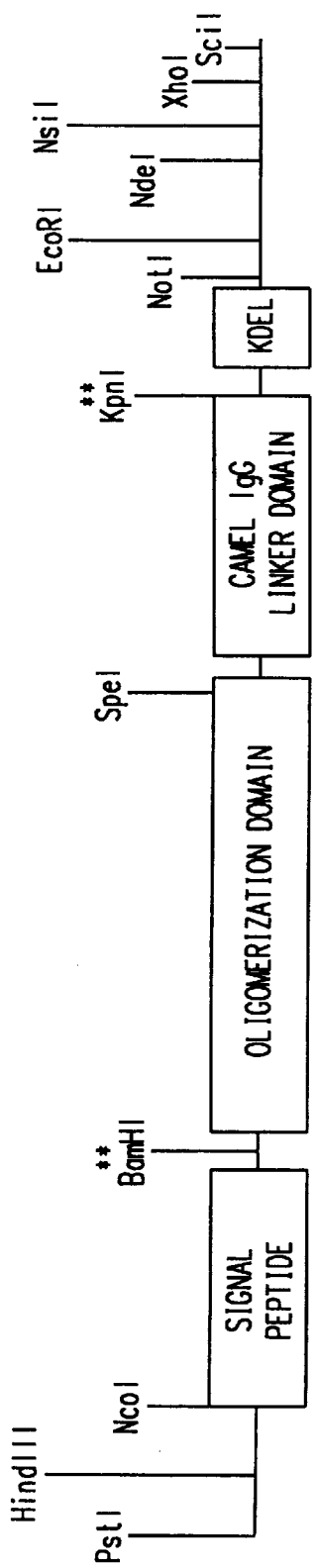
Figure 6B:
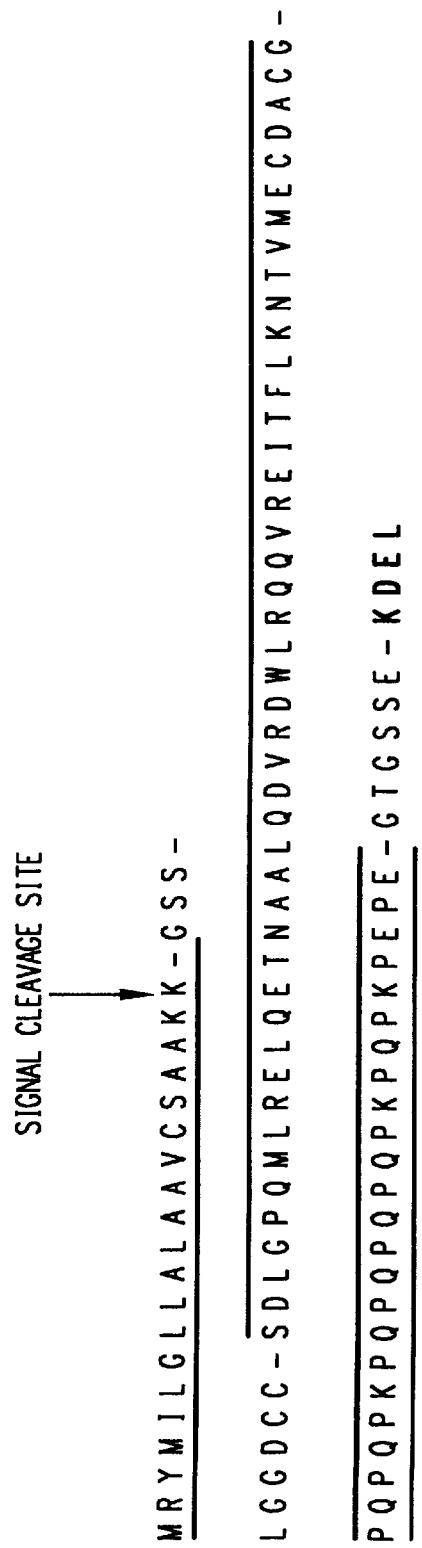
Figure 6C:
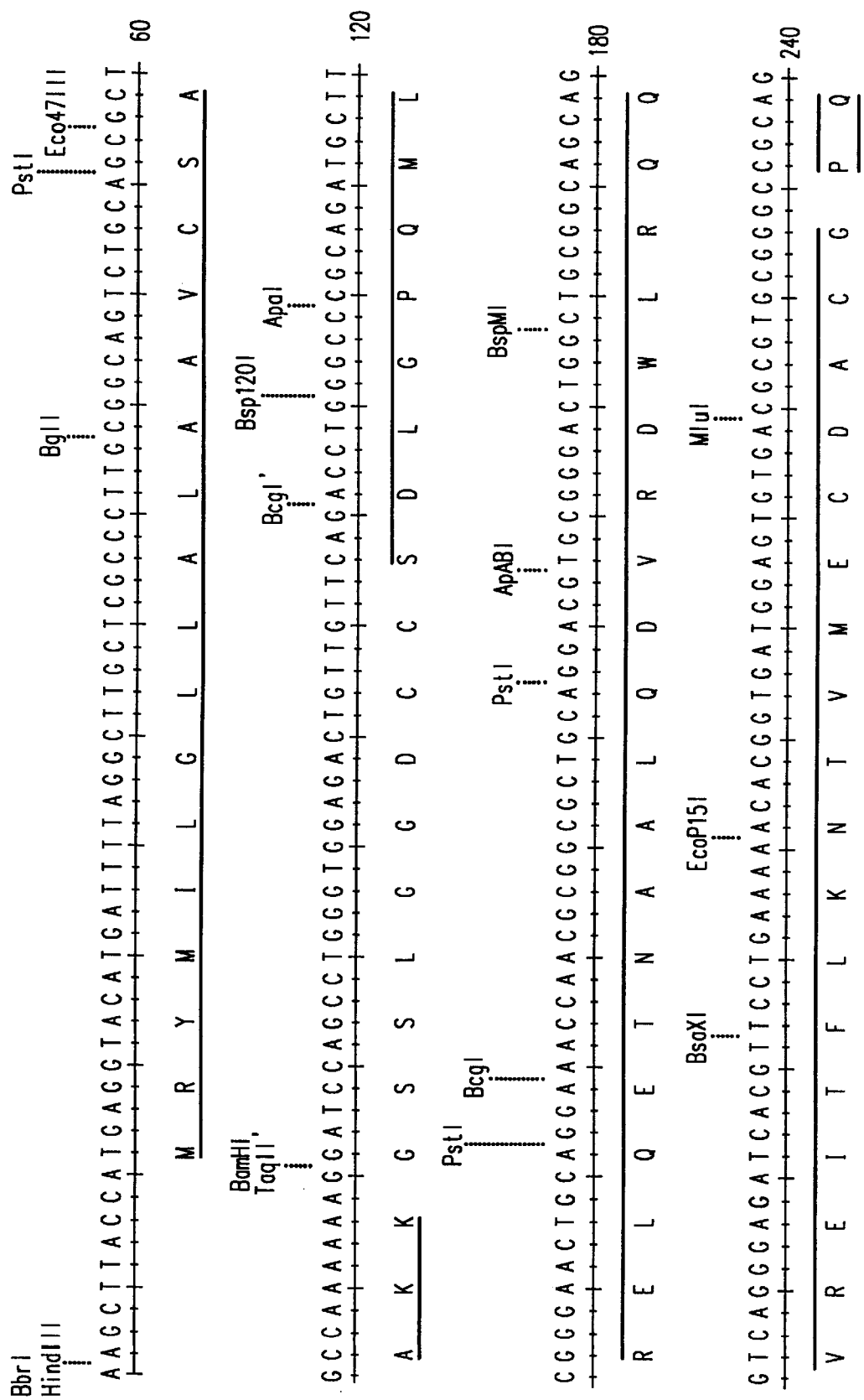
Figure 6D:
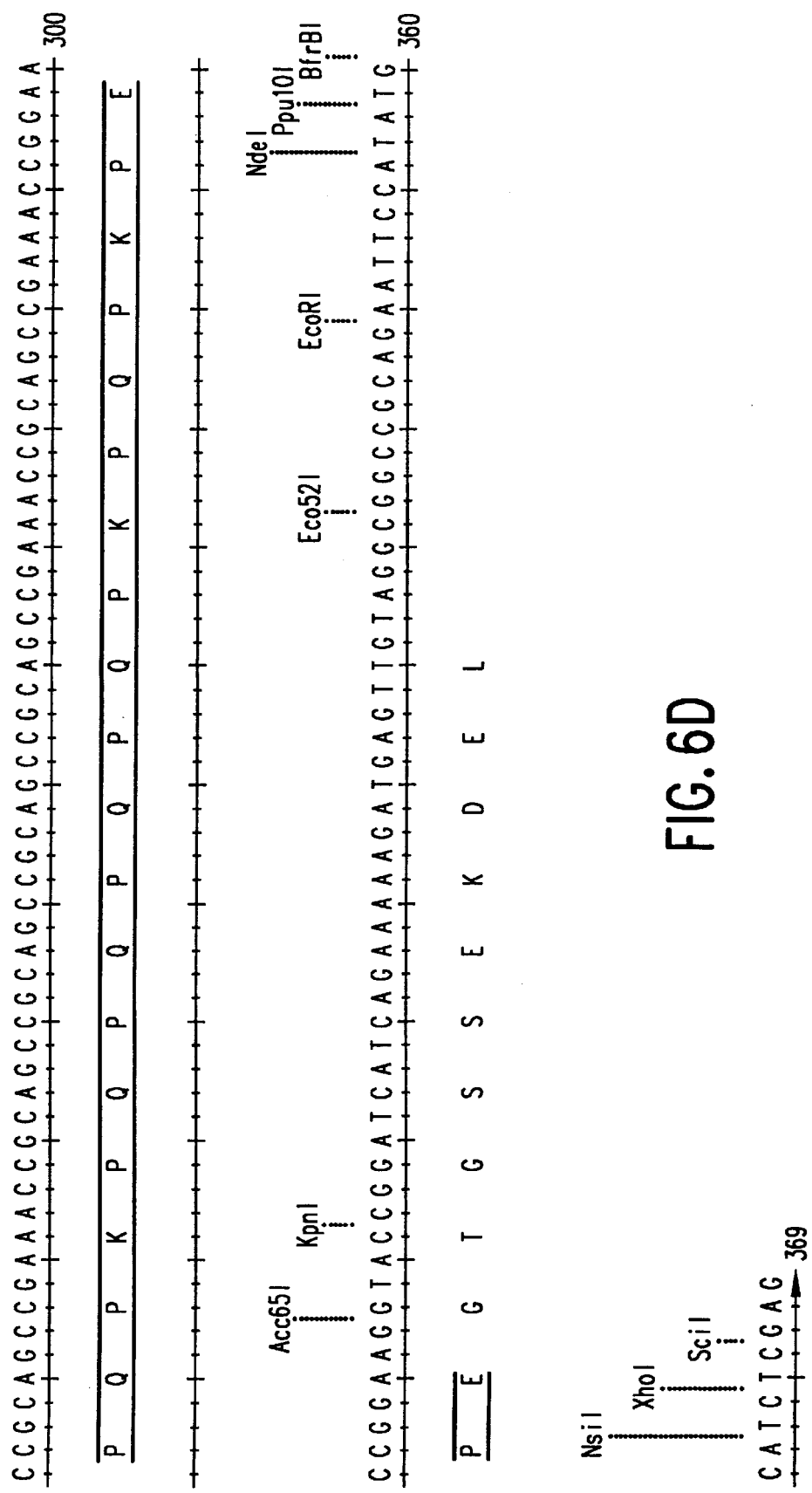
Figure 7A:
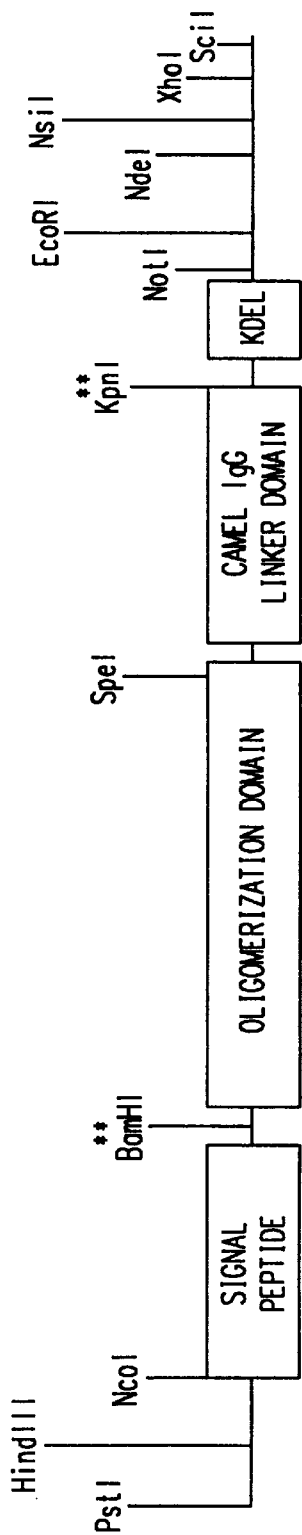
Figure 7B:
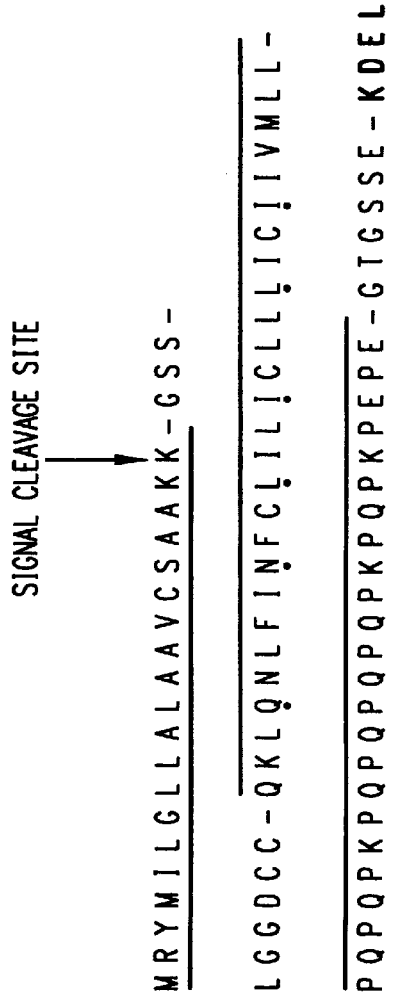
Figure 7C:
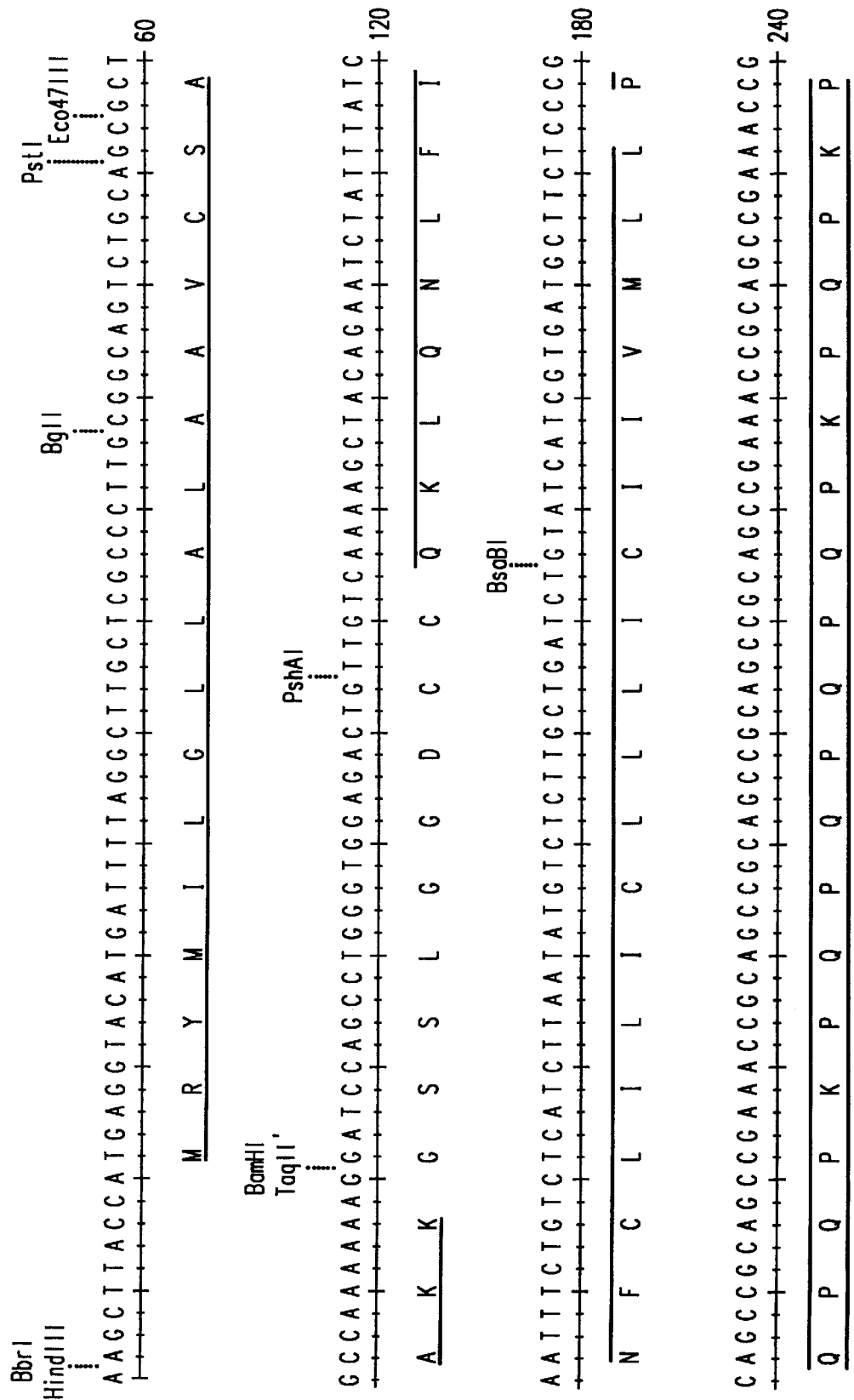
Figure 7D:
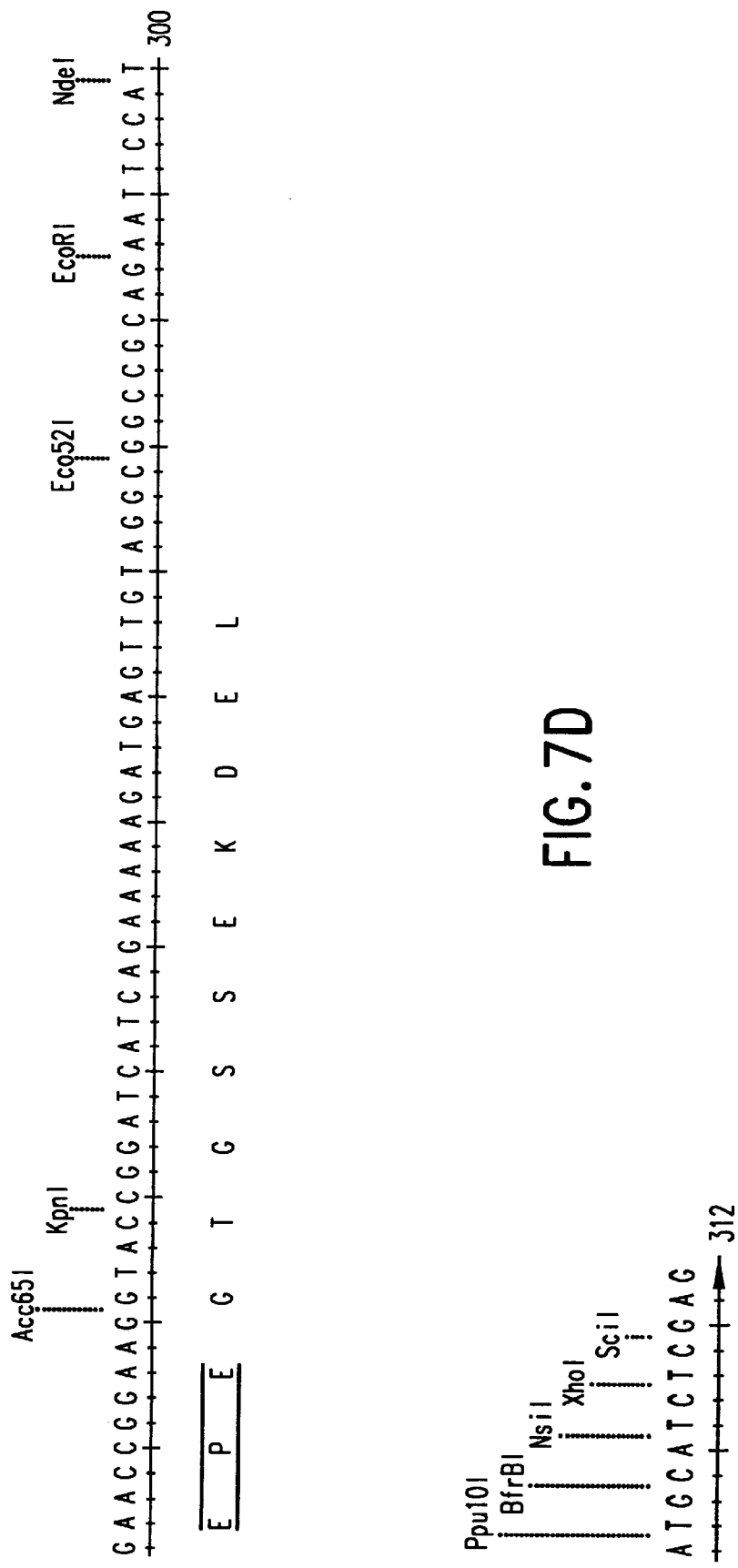
Figure 8A:
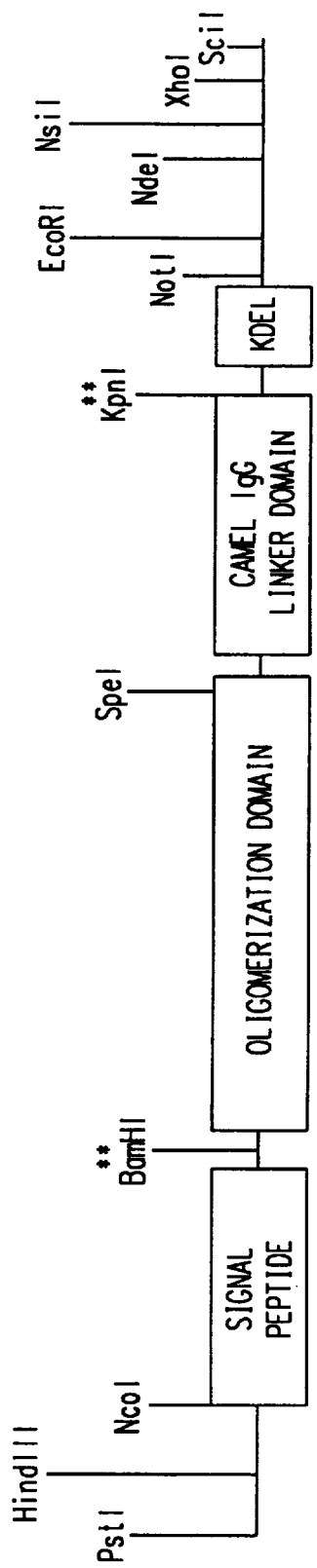
Figure 8B:
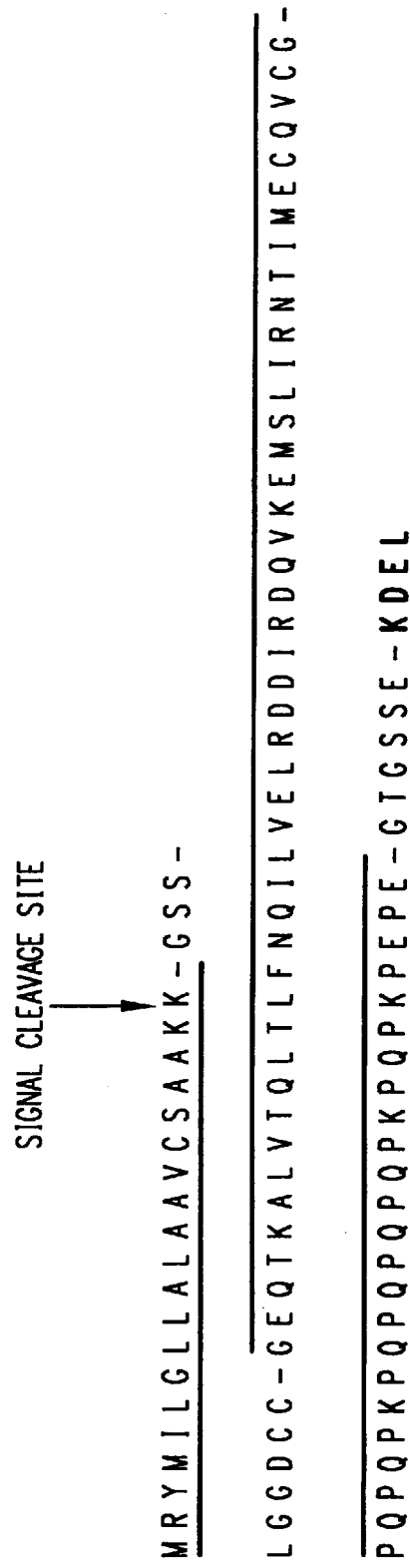
Figure 8C:
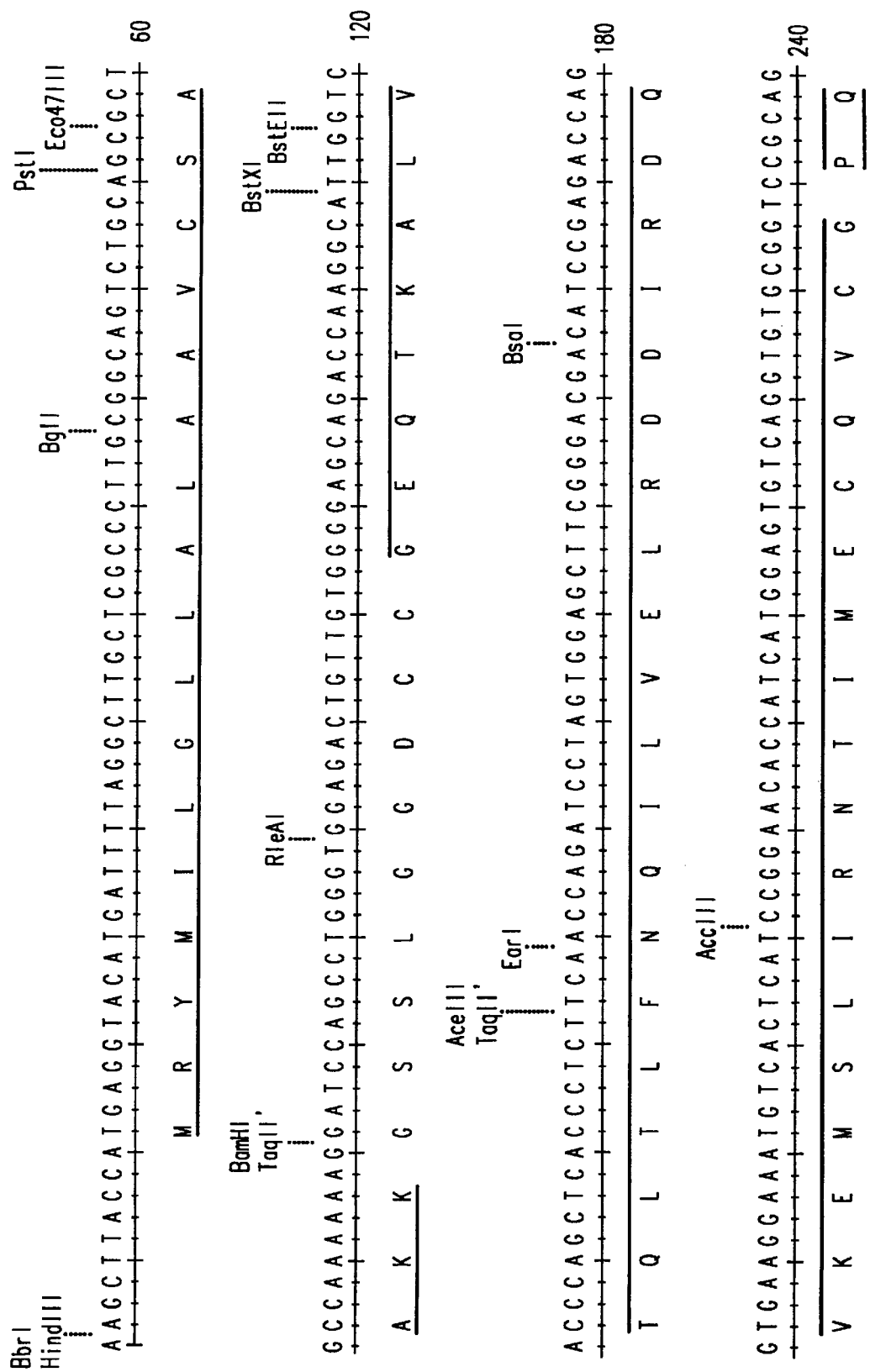
Figure 8D:
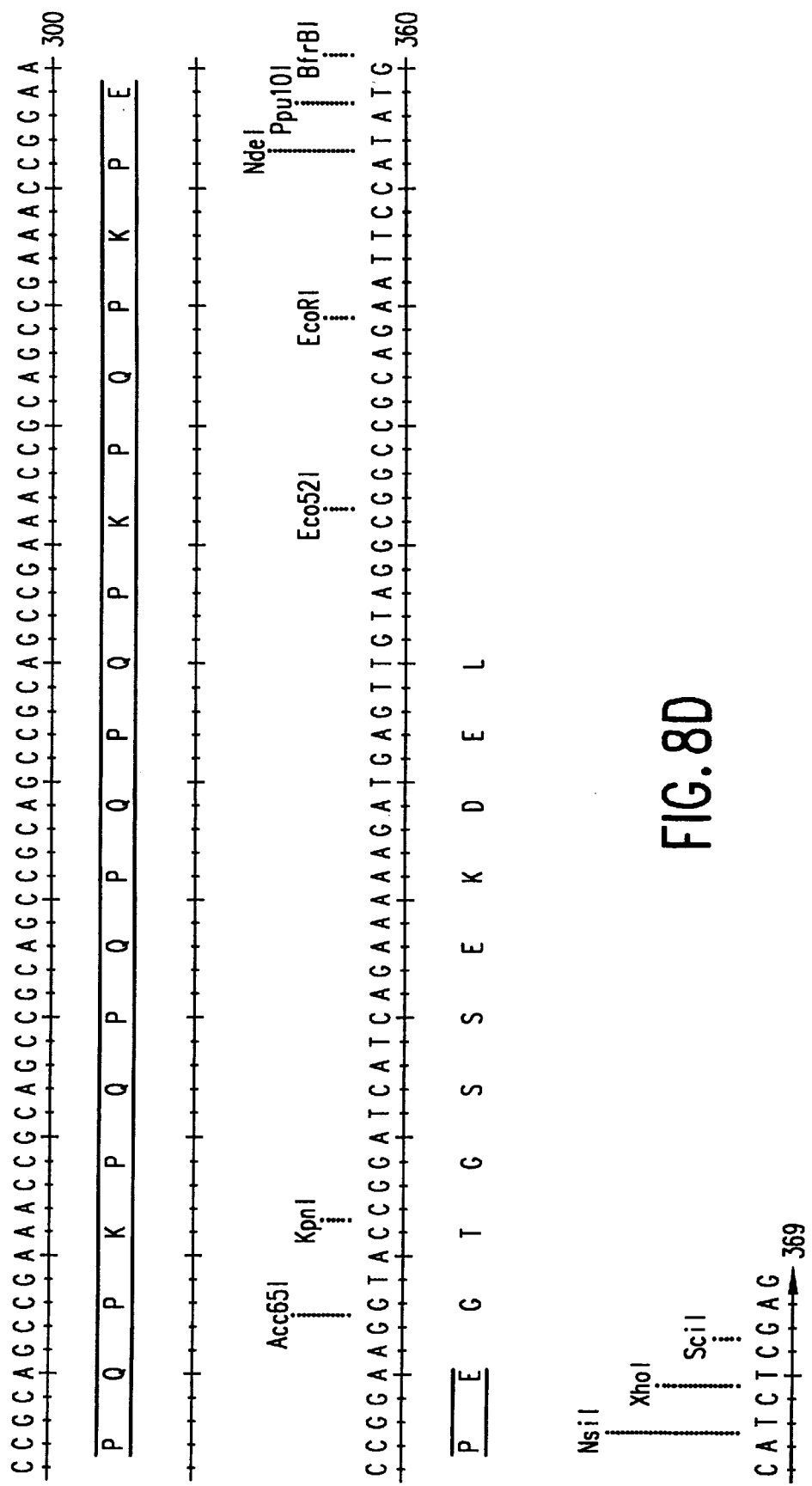
Figure 9A:
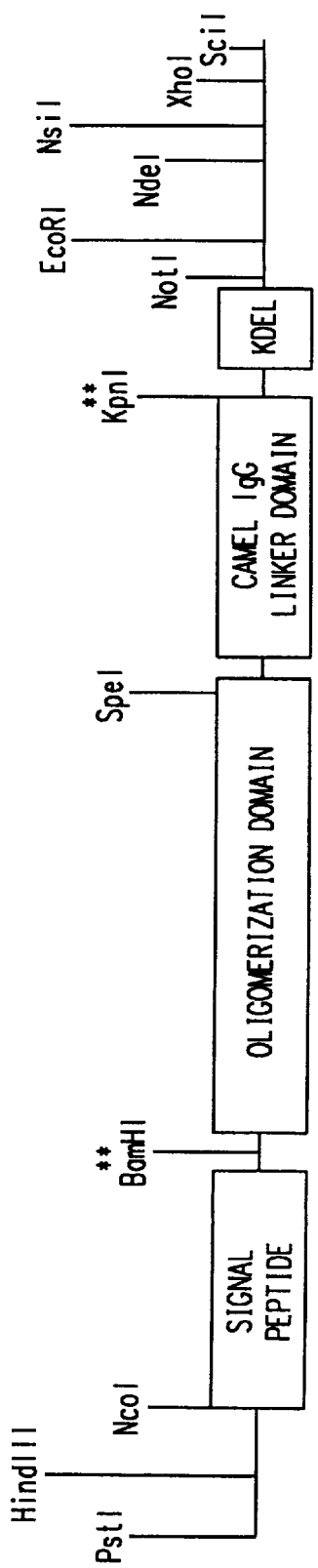
Figure 9B:
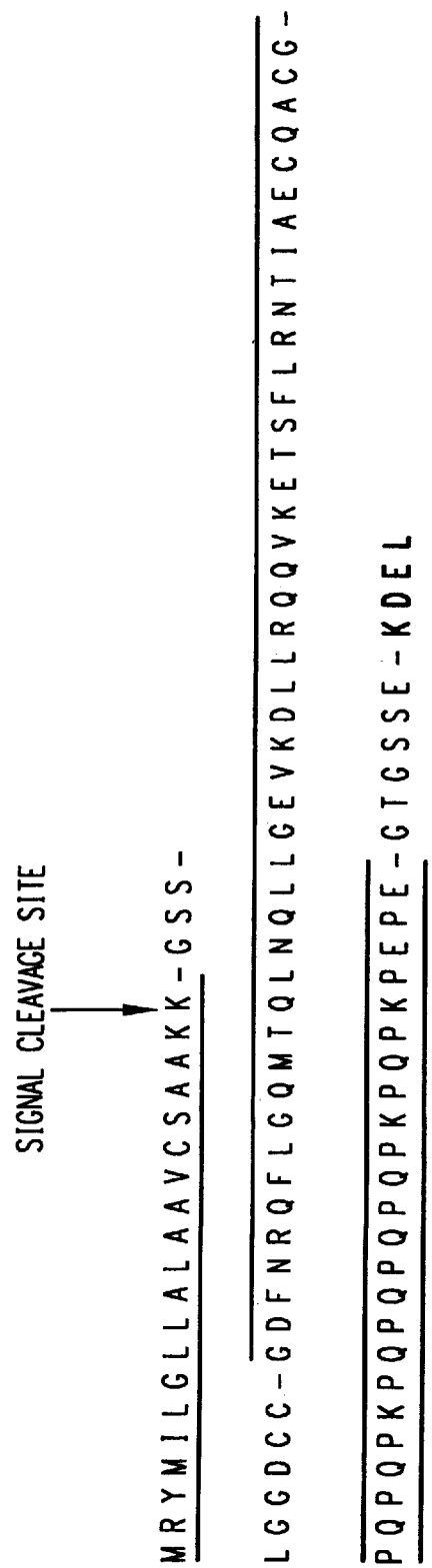
Figure 9C:
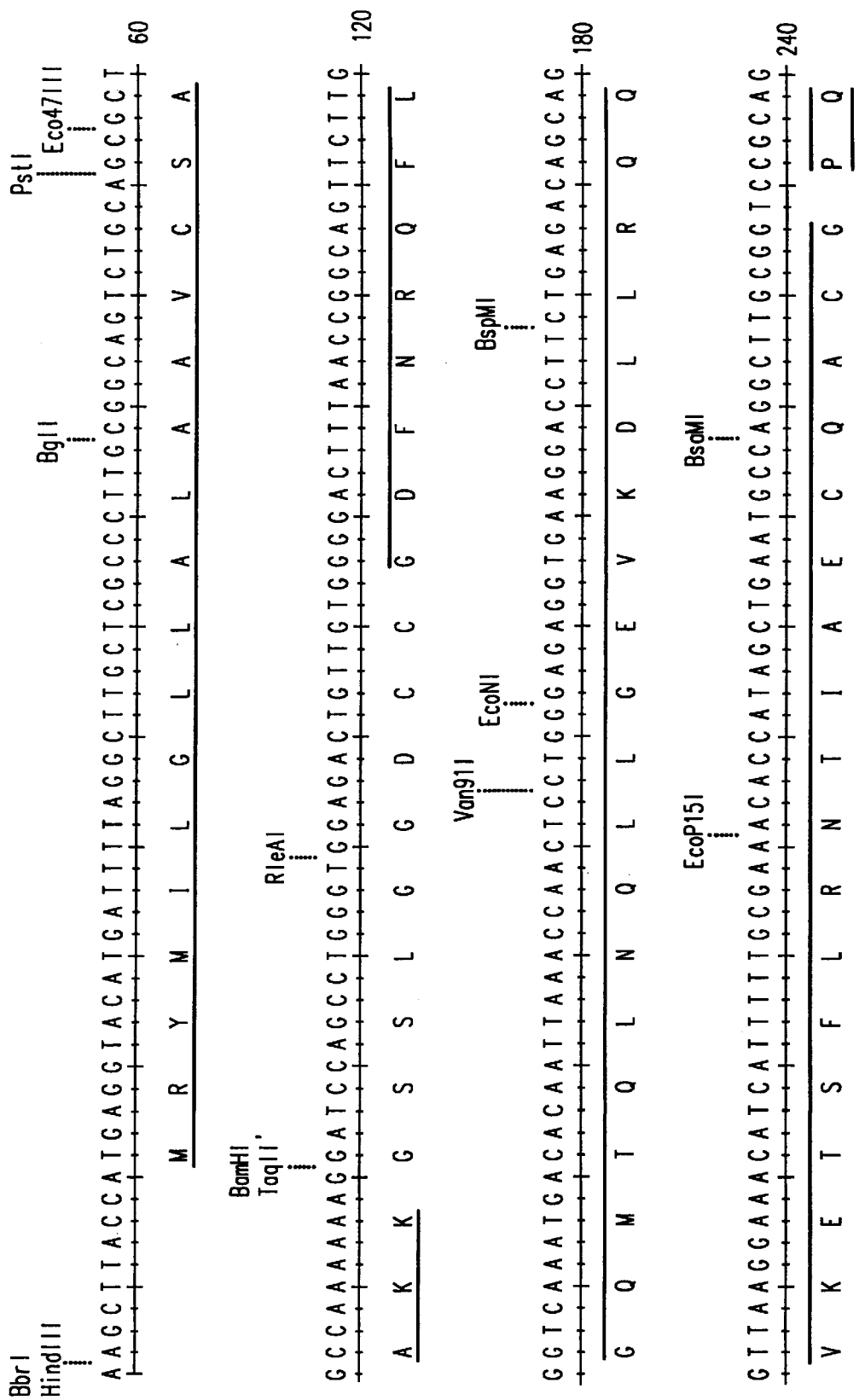
Figure 9D:
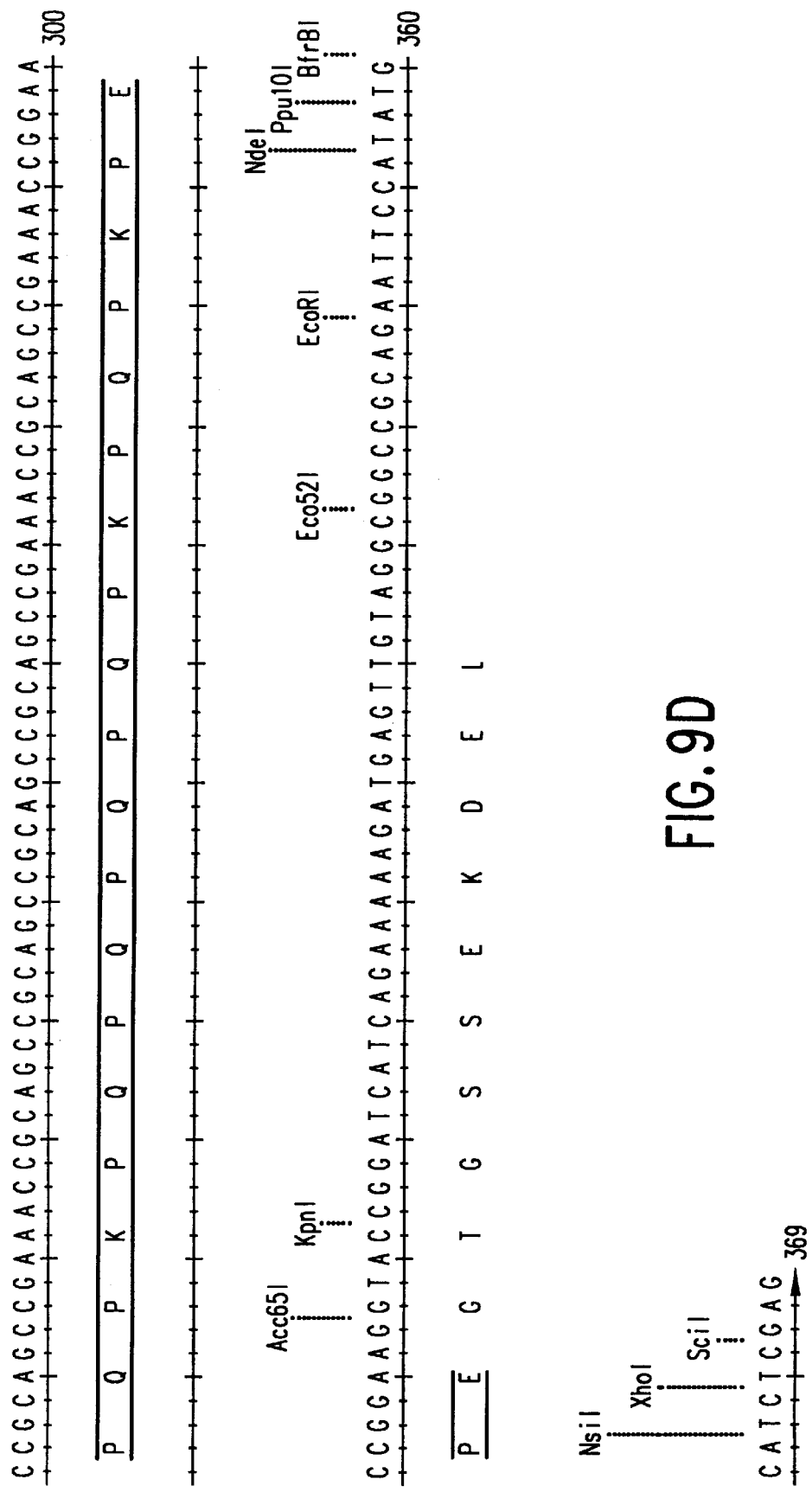
Figure 10A:
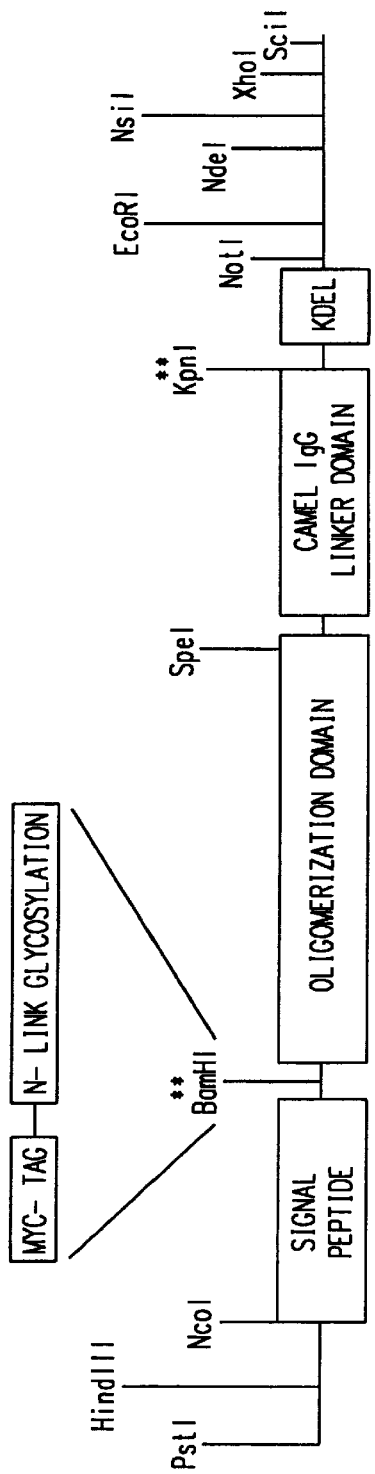
Figure 10B:
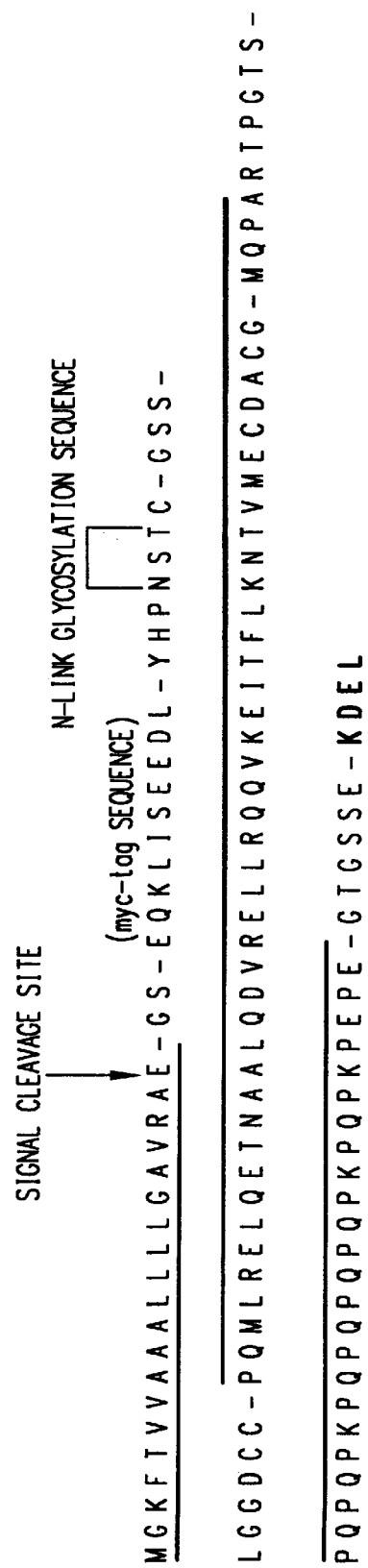
Figure 10C:
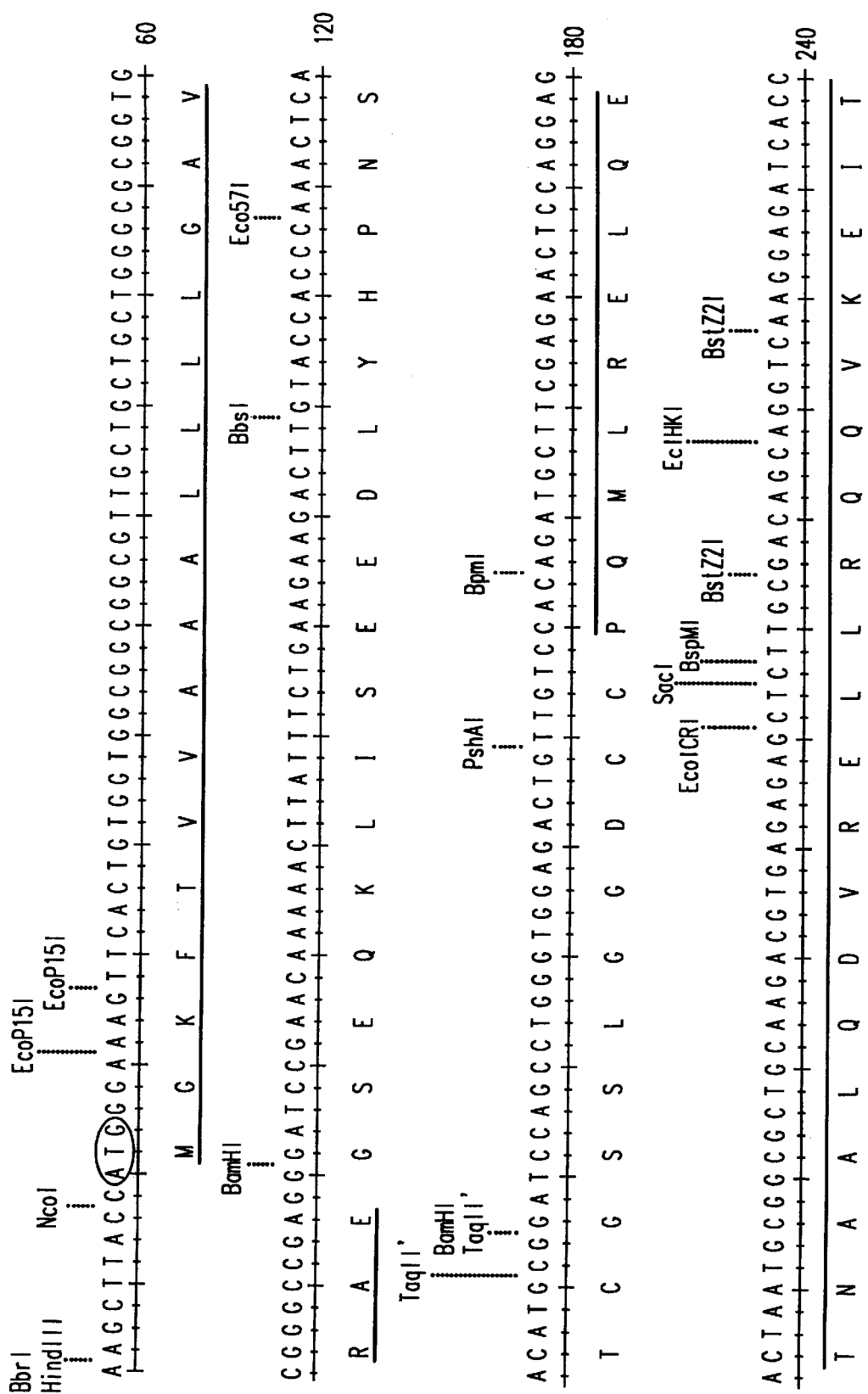
Figure 10D:
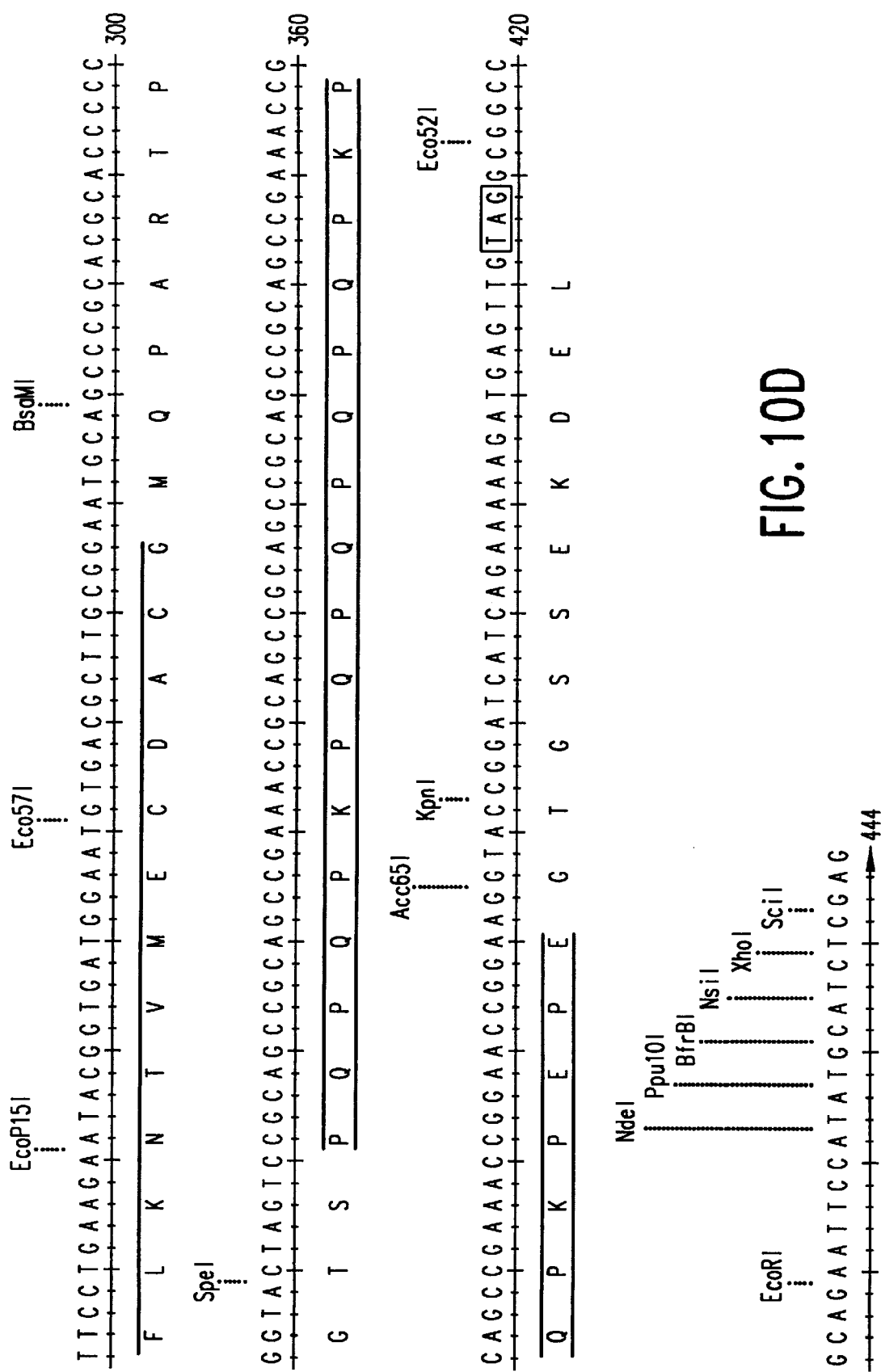

FIG. 1. (A) Schematic representation of a nucleic acid molecule encoding a KDEL receptor inhibitor protein comprising regions encoding (i) a cleavable signal peptide (in this example, from mouse BiP); (ii) the oligomerization domain of rat cartilage oligomeric matrix protein (COMP); (iii) a camel IgG linker domain; and (iii) the carboxy-terminal sequence KDEL (SEQ ID NO:37). Restriction endonuclease cleavage sites which may be used to incorporate the coding sequences into a number of vectors, known in the art, are shown. A double asterisk (**) denotes a Bam HI site located 3' to the signal peptide encoding sequence or a Kpn I site at the 5' end preceding the nucleotides encoding the amino acids KDEL (SEQ ID NO:37) into which, for example, nucleic acid encoding a peptide/target antigen may be inserted. (B) Amino acid sequence (single letter code) of KDEL receptor inhibitor protein encoded by the construct depicted in (A) (SEQ ID NO:13), showing the cleavable leader/signal peptide (underlined) plus linker (represented by amino acids-GSS-), the sub-sequence GDLA (SEQ ID NO:40) (from the rat COMP), the rat COMP pentamerization domain (overlined), and the camel IgG linker domain (underlined and overlined), linked to KDEL (SEQ ID NO:37). (C-D) Nucleic acid sequence of the rat COMP-KDEL construct shown in (A) (SEQ ID NO:14).

FIG. 2.(A) Schematic representation of a nucleic acid molecule encoding a KDEL receptor inhibitor protein comprising regions encoding (i) a cleavable signal peptide (from mouse BiP); (ii) the oligomerization domain of rat cartilage oligomeric matrix protein (COMP); (iii) a camel IgG linker domain; and (iii) the carboxy-terminal sequence KDEL (SEQ ID NO:37). Restriction endonuclease cleavage sites which may be used to incorporate the coding sequences into a number of vectors, known in the art, are shown. A double asterisk (**) denotes a Bam HI site located 3' to the signal peptide encoding sequence or a Kpn I site at the 5' end preceding the nucleotides encoding the amino acids KDEL into which, for example, nucleic acid encoding a peptide/target antigen may be inserted. (B) Amino acid sequence (single letter code) of KDEL receptor inhibitor protein encoded by the construct depicted in (A) (SEQ ID NO:15), showing the cleavable leader/signal peptide (underlined) plus linker (represented by amino acids-GSS-), the sub-sequence GDCC SEQ ID NO:41 of the rat COMP sub-sequence shown in FIG. 1B which provides increased stability via disulfide bonds); the rat COMP pentamerization domain (overlined), and the camel IgG linker domain (underlined and overlined), linked to KDEL (SEQ ID NO:37). (C-D) Nucleic acid sequence of the rat COMP-KDEL construct shown in (A) (SEQ ID NO:16).

FIG. 3.(A) Schematic representation of a nucleic acid molecule encoding a KDEL receptor inhibitor protein comprising regions encoding (i) a cleavable signal peptide (from mouse BiP); (ii) the oligomerization domain of mouse thromospondin 3 trimerization domain (TSP3); (iii) a camel IgG linker domain; and (iii) the carboxy-terminal sequence KDEL (SEQ ID NO:37). Restriction endonuclease cleavage sites which may be used to incorporate the coding sequences into a number of vectors, known in the art, are shown. A double asterisk (**) denotes a Bam HI site located 3' to the signal peptide encoding sequence or a Kpn I site at the 5' end preceding the nucleotides encoding the amino acids KDEL (SEQ ID NO:37) into which, for example, nucleic acid encoding a peptide/target antigen may be inserted. (B) Amino acid sequence (single letter code) of KDEL receptor inhibitor protein shown in (A) (SEQ ID NO:17), indicating the leader/signal peptide (underlined) plus linker (represented by amino acids-GSS-), the sub-sequence GDCC SEQ ID NO:41 (an alteration of the rat COMP sub-sequence shown in FIG. 1B which provides increased stability via disulfide bonds), the mouse TSP3 trimerization domain (overlined), the camel IgG linker domain (overlined and underlined) and KDEL. (C-D) Nucleic acid sequence of the mouse TSP3-KDEL construct shown in (A) (SEQ ID NO:18), indicating the translation start site (circled) and termination site (boxed).

FIG. 4.(A) Schematic representation of a nucleic acid molecule encoding a KDEL receptor inhibitor protein comprising regions encoding (i) a cleavable signal peptide (from mouse BiP); (ii) the oligomerization domain of mouse thrombospondin 3 trimerization domain (TSP3); (iii) a camel IgG linker domain; and (iii) the carboxy-terminal sequence KDEL (SEQ ID NO:37). Restriction endonuclease cleavage sites which may be used to incorporate the coding sequences into a number of vectors, known in the art, are shown. A double asterisk (**) denotes a Bam HI site located 3' to the signal peptide encoding sequence or a Kpn I site at the 5' end preceding the nucleotides encoding the amino acids KDEL (SEQ ID NO:37) into which, for example, nucleic acid encoding a peptide/target antigen may be inserted. (B) Amino acid sequence (single letter code) of KDEL receptor inhibitor protein shown in (A) (SEQ ID NO:17), indicating the leader/signal peptide (underlined) plus linker (represented by amino acids-GSS-), the sub-sequence GDCC (SEQ ID NO:41), an alteration of the rat COMP sub-sequence shown in FIG. 1B which provides increased stability via disulfide bonds), the mouse TSP3 trimerization domain (overlined, including an additional sub-sequence GEQT (SEQ ID NO:42) at the 5' end relative to FIG. 3B), the camel IgG linker domain (overlined and underlined) and KDEL (SEQ ID NO:37). (C-D) Nucleic acid sequence of the mouse TSP3-KDEL construct shown in (A) (SEQ ID NO:20), indicating the translation start site (circled) and termination site (boxed).

FIG. 5. (A) Schematic representation of a nucleic acid molecule encoding a KDEL receptor inhibitor protein comprising regions encoding (i) a cleavable signal peptide (from mouse BiP); (ii) the oligomerization domain of Xenopus thrombospondin 4 trimerization domain (TSP4); (iii) a camel IgG linker domain; and (iii) the carboxy-terminal sequence KDEL (SEQ ID NO:37). Restriction endonuclease cleavage sites which may be used to incorporate the coding sequences into a number of vectors, known in the art, are shown. A double asterisk (**) denotes a Bam HI site located 3' to the signal peptide encoding sequence or a Kpn I site at the 5' end preceding the nucleotides encoding the amino acids KDEL (SEQ ID NO:37) into which, for example, nucleic acid encoding a peptide/target antigen may be inserted. (B) Amino acid sequence (single letter code) of KDEL receptor inhibitor protein shown in (A) (SEQ ID NO:21), indicating the leader/signal peptide (underlined) plus linker (represented by the amino acids-GSS-), the sub-sequence GDCC (SEQ ID NO:41), the Xenopus TSP4 trimerization domain (overlined), the camel IgG linker domain (overlined and underlined) and KDEL. (C-D) Nucleic acid sequence of the Xenopus TSP4-KDEL (SEQ ID NO:37) construct shown in (A) (SEQ ID NO:22), indicating the translation start site (circled) and termination site (boxed).

FIG. 6.(A) Schematic representation of a nucleic acid molecule encoding a KDEL (SEQ ID NO:37) receptor inhibitor protein comprising regions encoding (i) a cleavable signal peptide (in this example from adenovirus E3/19 kDa protein); (ii) the oligomerization domain of human cartilage oligomeric matrix protein (COMP); (iii) a camel IgG linker domain; and (iii) the carboxy-terminal sequence KDEL. Restriction endonuclease cleavage sites which may be used to incorporate the coding sequences into a number of vectors, known in the art, are shown. A double asterisk (**) denotes a Bam HI site located 3' to the signal peptide encoding sequence or a Kpn I site at the 5' end preceding the nucleotides encoding the amino acids KDEL into which, for example, nucleic acid encoding a peptide/target antigen may be inserted. (B) Amino acid sequence (single letter code) of KDEL receptor inhibitor protein shown in (A) (SEQ ID NO:23), indicating the leader/signal peptide (underlined) plus linker (represented by the amino acids-GSS-), the sub-sequence GDCC (SEQ ID NO:41), the human COMP pentamerization domain (overlined), the camel IgG linker domain (overlined and underlined) and KDEL (SEQ ID NO:37). (C-D) Nucleic acid sequence of the human COMP-KDEL construct shown in (A) (SEQ ID NO:24), indicating the translation start site (circled) and termination site (boxed).

FIG. 7.(A) Schematic representation of a nucleic acid molecule encoding a KDEL receptor inhibitor protein comprising regions encoding (i) a cleavable signal peptide (from adenovirus E3/19 kDa protein); (ii) the oligomerization domain of human phospholamban (PLB); (iii) a camel IgG linker domain; and (iii) the carboxy-terminal sequence KDEL (SEQ ID NO:37). Restriction endonuclease cleavage sites which may be used to incorporate the coding sequences into a number of vectors, known in the art, are shown. A double asterisk (**) denotes a Bam HI site located 3' to the signal peptide encoding sequence or a Kpn I site at the 5' end preceding the nucleotides encoding the amino acids KDEL into which, for example, nucleic acid encoding a peptide/target antigen may be inserted. (B) Amino acid sequence (single letter code) of KDEL receptor inhibitor protein shown in (A) (SEQ ID NO:25), indicating the leader/signal peptide (underlined) plus linker (represented by amino acids-GSS-), the sub-sequence GDCC (SEQ ID NO:41), the human PLB pentamerization domain (overlined, residues critical for pentamer formation marked by a dot), the camel IgG linker domain (overlined and underlined) and KDEL (SEQ ID NO:37). (C-D) Nucleic acid sequence of the human PLB-KDEL construct shown in (A) (SEQ ID NO:26), indicating the translation start site (circled) and termination site (boxed).

FIG. 8.(A) Schematic representation of a nucleic acid molecule encoding a KDEL receptor inhibitor protein comprising regions encoding (i) a cleavable signal peptide (from adenovirus E3/19 kDa protein); (ii) the oligomerization domain of human thrombospondin 3 (TSP3); (iii) a camel IgG linker domain; and (iii) the carboxy-terminal sequence KDEL (SEQ ID NO:37). Restriction endonuclease cleavage sites which may be used to incorporate the coding sequences into a number of vectors, known in the art, are shown. A double asterisk (**) denotes a Bam HI site located 3' to the signal peptide encoding sequence or a Kpn I site at the 5' end preceding the nucleotides encoding the amino acids KDEL (SEQ ID NO:37) into which, for example, nucleic acid encoding a peptide/target antigen may be inserted. (B) Amino acid sequence (single letter code) of KDEL receptor inhibitor protein shown in (A) (SEQ ID NO:27), indicating the leader/signal peptide (underlined) plus linker (represented by amino acids-GSS-), the sub-sequence GDCC (SEQ ID NO:41), the human TSP3 trimerization domain (overlined), the camel IgG linker domain (overlined and underlined) and KDEL (SEQ ID NO:37). (C-D) Nucleic acid sequence of the human TSP3-KDEL construct shown in (A) (SEQ ID NO:28), indicating the translation start site (circled) and termination site (boxed).

FIG. 9.(A) Schematic representation of a nucleic acid molecule encoding a KDEL receptor inhibitor protein comprising regions encoding (i) a cleavable signal peptide (from adenovirus E3/19 kDa protein); (ii) the oligomerization domain of human thrombospondin 4 (TSP4); (iii) a camel IgG linker domain; and (iii) the carboxy-terminal sequence KDEL (SEQ ID NO:37). Restriction endonuclease cleavage sites which may be used to incorporate the coding sequences into a number of vectors, known in the art, are shown. A double asterisk (**) denotes a Bam HI site located 3' to the signal peptide encoding sequence or a Kpn I site at the 5' end preceding the nucleotides encoding the amino acids KDEL (SEQ ID NO:37 into which, for example, nucleic acid encoding a peptide/target antigen may be inserted. (B) Amino acid sequence (single letter code) of KDEL receptor inhibitor protein shown in (A) (SEQ ID NO:29), indicating the leader/signal peptide (underlined) plus linker (represented by amino acids-GSS-), the sub-sequence GDCC (SEQ ID NO:41), the human TSP4 trimerization domain (overlined), the camel IgG linker domain (overlined and underlined) and KDEL (SEQ ID NO:37). (C-D) Nucleic acid sequence of the human TSP4-KDEL construct shown in (A) (SEQ ID NO:30), indicating the translation start site (circled) and termination site (boxed).

FIG. 10.(A) Schematic representation of a nucleic acid molecule encoding a KDEL inhibitor protein having (i) a cleavable signal peptide from mouse BiP; (ii) a myc-tag; (iii) an N-linked glycosylation sequence; (iv) the oligomerization domain of the rat cartilage oligomerization protein; (iv) a camel IgG linker domain; and (v) the carboxy terminal sequence KDEL. (B) (SEQ ID NO:37)(B) Amino acid sequence (single letter code) of KDEL (SEQ ID NO:37). (C-D) receptor inhibitor protein shown in (A) (SEQ ID NO:34), indicating the leader/signal peptide (underlined), myc-tag, N-linked glycosylation sequence, linker (represented by amino acids-GSS-), the sub-sequence GDCC, the rat COMP domain (overlined), the camel IgG linker domain (overlined and underlined) and KDEL. (C-D) Nucleic acid sequence of the KDEL construct shown in (A) (SEQ ID NO:35), indicating the translation start site (circled) and termination site (boxed).

5. DETAILED DESCRIPTION OF THE INVENTION

For purposes of clarity of presentation and not by way of limitation, the detailed description of the invention is divided into the following subsections:

(i) KDEL receptor inhibitor proteins; and (ii) uses of KDEL receptor inhibitors.

5.1. KDEL RECEPTOR INHIBITOR PROTEINS

The present invention provides for a protein comprising a plurality of amino acid sequences which bind to a KDEL receptor (hereafter referred to as a "KDELr inhibitor protein"). By containing a plurality of such sequences, said protein may favorably compete with naturally occurring proteins which bind to the KDEL receptor but which contain a single binding sequence. In preferred, nonlimiting embodiments, the KDELr inhibitor protein is oligomeric, comprising a plurality of subunit proteins each of which comprise, at their carboxy terminal end, a sequence which binds to a KDEL receptor.

The term "KDEL receptor", as used herein, refers to a protein which selectively and specifically binds to a carboxy-terminal KDEL (SEQ ID NO:37) sequence in proteins, and which participates in the redistribution of bound proteins from the Golgi complex to the endoplasmic reticulum. In specific, nonlimiting embodiments, KDEL receptors include the protein encoded by ERD2 in *Saccharomyces cerevesiae* ("ERD2") as well as its human homolog ("hERD2"), as well as structurally and functionally homologous proteins, such as ELP-1, which is 83 percent identical to human ERD-2 (Lewis et al., 1990, Nature 348:162–162; Semenza et al., 1990, Cell 61:1349–1357; Lewis and Pelham, 1992, J. Mol. Biol. 226:913–916; Lewis and Pelham, 1992, Cell 68:353–364; Hsu et al., 1992, Cell 69:625–635).

In specific, nonlimiting embodiments, the amino acid sequence which binds to the KDEL receptor is X-Asp Glu Leu ("XDEL"; SEQ ID NO:37), where X may be any amino acid, preferably lysine or histidine and most preferably lysine, and is located at the carboxy terminus such that the ultimate C-terminal residue is the leucine of X-Asp-Glu-Leu (SEQ ID NO:37). In specific nonlimiting embodiments of the invention, the carboxy terminal sequence may be Ser-Glu-Lys-Asp-Glu-Leu ("SEKDEL" SEQ ID NO:39). Additional amino acid sequences which may bind to the KDEL receptor may be identified by testing the ability of such sequences to compete with Lys-Asp-Glu-Leu (KDEL SEQ ID NO:37) for binding to the KDEL receptor in a cell (see, for example, experiments described in Munro and Pelham, 1987, Cell 48:899–907) or under comparable conditions in vitro.

Where the KDELr inhibitor protein is oligomeric, it may comprise a plurality of subunits, wherein the subunits may be structurally the same (i.e., a "homooligomer") or different (i.e., a "heterooligomer"). Each subunit may comprise a carboxy terminus which binds to a KDEL receptor, and the remainder of the subunit, or a portion thereof, may permit a means for the association between subunits and the formation of the oligomer. Subunits may be covalently or noncovalently joined together. Where subunits are covalently joined, linkages may result from disulfide bonds, oxidized carbohydrate residues, or crosslinking agents, to name a few nonlimiting examples.

In preferred embodiments of the invention, an amino acid sequence which binds to the KDEL receptor may be incorporated as the carboxy terminus in a protein subunit of an oligomeric protein or portion thereof. Suitable known oligomers may include immunoglobulin molecules; especially preferred, however, are smaller oligomeric molecules, including, but not limited to, pentamers formed via the oligomerization domain of a cartilage oligomeric matrix protein ("COMP", which has been used to produce a high avidity binding protein termed a "peptabody", described in Terskikh et al., 1997, Proc. Natl. Acad. Sci. U.S.A. 94:1663–1668).

Thus, in specific, nonlimiting examples, the present invention provides for a KDELr inhibitor protein formed via association between a plurality of subunits, each comprising the oligomerization domain of a COMP or a homologous oligomeric protein such as thrombospondin 3 ("TSP3", which is trimeric), thrombospondin 4 ("TSP 4", which is trimeric) or phospholamban ("PLB", which is pentameric). As such, the present invention provides for an oligomeric KDELr inhibitor protein comprising a plurality of subunits, wherein each subunit comprises an oligomerization domain and has, at its carboxy terminus, a region which binds to a KDEL receptor, for example, a region having, at its carboxy terminus, the XDEL (SEQ ID NO:38) amino acid sequence referred to above. In preferred nonlimiting embodiments of the invention, the region which binds to a KDEL receptor has the amino acid sequence Lys Asp Glu Leu (SEQ ID NO:37), and the oligomerization domain has an amino acid sequence selected from the following amino acid sequences (Malashkevick et al., 1996, Science 274:761–765), or a subfragment or homolog thereof which forms an oligomer under conditions as set forth in Efimov et al., 1994, FEBS Letts 341:54–58 and Efimov et al., 1996, Proteins 24:259.

(1) COMP (rat, res. 27–72) Gly-Asp-Leu-Ala-Pro-Gln-Met-Leu-Arg-Glu-Leu-Gln-Glu-Thr-Asn-Ala-Ala-Leu-Gln-Asp-Val-Arg-Glu-Leu-Leu-Arg-Gln—Gln-Val-Lys-Glu-Ile-Thr-Phe-Leu-Lys-Asn-Thr-Val-Met-Glu-Cys-Asp-Ala-Cys-Gly (SEQ ID NO: 1);

(2) COMP (human) Ser-Asp-Leu-Gly-Pro-Gln-Met-Leu-Arg-Glu-Leu—Gln-Glu-Thr-Asn-Ala-Ala-Leu-Gln- Asp-Val-Arg-Asp-Trp-Leu-Arg-Gln-Gln-Val-Arg-Glu-Ile-Thr-Phe—Leu-Lys-Asn-Thr-Val-Met-Glu-Cys-Asp-Ala-Cys-Gly (SEQ ID NO:2);

(3) TSP3 (mouse) Gly-Glu-Gln-Thr-Lys-Ala-Leu-Val-Thr-Gln-Leu-Thr-Leu-Phe—Asn-Gln-Ile-Leu-Val-Glu-Leu-Ar-Asp-Asp-Ile-Arg-Asp-Gln-Val-Lys-Glu-Met-Ser-Leu-Ile—Arg-Asn-Thr-Ile-Met-Glu-Cys-Gln-Val-Cys-Gly (SEQ ID NO:3);

(4) TSP3 (human) Gly-Glu-Gln-Thr-Lys-Ala-Leu-Val-Thr-Gln-Leu-Thr-Leu-Phe—Asn-Gln-Ile-Leu-Val-Glu-Leu-Ar-Asp-Asp-Ile-Arg-Asp-Gln-Val-Lys-Glu-Met-Ser-Leu-Ile—Arg-Asn-Thr-Ile-Met-Glu-Cys-Gln-Val-Cys-Gly (SEQ ID NO:4);

(5) TSP4 (human) Gly-Asp-Phe-Asn-Arg-Gln-Phe-Leu-Gly-Gln-Met-Thr-Gln—Leu-Asn-Gln-Leu-Leu-Gly-Glu-Val-Lys-Asp-Leu-Leu-Arg-Gln-Gln-Val-Lys-Glu-Thr-Ser-Phe—Leu-Arg-Asn-Thr-Ile-Ala-Glu-Cys-Gln-Ala-Cys-Gly (SEQ ID NO:5);

(6) TSP4 (Xenopus) Gly-Asp-Val-Ser-Arg-Gln-Leu-Ile-Gly-Gln-Ile-Thr-Gln-Met—Asn-Gln-Met-Leu-Gly-Glu-Leu-Arg-Asp-Val-Met-Arg-Gln-Gln-Val-Lys-Glu-Thr-Met-Phe—Leu-Arg-Asn-Thr-Ile-Ala-Glu-Cys-Gln-Ala-Cys-Gly (SEQ ID NO:6); and (7) PLB (human, residues 26–52) Gln-Lys-Leu-Gln-Asn-Leu-Phe-Ile-Asn-Phe—Cys-Leu-Ile-Leu-Ile-Cys-Leu-Leu-Leu-Ile-Cys-Ile-Ile-Val-Met-Leu-Leu (SEQ ID NO:7).

The foregoing sequences may, for example, be altered by deletion, insertion, or substitution, provided that they remain capable of forming an oligomer under comparable conditions.

KDELr inhibitor proteins may be prepared by any method known in the art, using either chemical synthesis or genetic engineering techniques. Accordingly, the present invention provides for nucleic acids comprising regions encoding a KDELr inhibitor protein of the invention or a subunit thereof, operably linked to suitable elements which facilitate the expression of the protein, and comprised in a nucleic acid vector. Suitable vectors include, but are not limited to, herpes simplex viral based vectors such as pHSV1 (Geller et al., 1990, Proc. Natl. Acad. Sci. U.S.A. 87:8950–8954); retroviral vectors such as MFG (Jaffee et al., 1993, Cancer Res. 53:2221–2226), and in particular Moloney retroviral vectors such as LN, LNSX, LNCX, LXSN (Miller and Rosman, 1989, Biotechniques 7:980–989) and semliki forest virus ("SFV") vectors; vaccinia viral vectors such as MVA (Sutter and Moss, 1992, Proc. Natl. Acad. Sci. U.S.A. 89:10847–10851); adenovirus vectors such as pJM17 (Ali et al., 1994, Gene Therapy 1:367–384; Berker, 1988, Biotechniques 6:616–624; Wand and Finer, 1996, Nature Medicine 2:714–716); adeno-associated virus vectors such as AAV/neo (Mura-Cacho et al., 1992, J. Immunother. 11:231–237); lentivirus vectors (Zufferey et al., 1997, Nature Biotechnology 15:871–875; pET 11a, pET3a, pET11d, pET3d, pET22d, and pET12a (Novagen); plasmid AH5 (which contains the SV40 origin and the adenovirus major late promoter); pRC/CMV (In Vitrogen, Carlsbad, Calif.); pCMU II (Paabo et al., 1986, EMBO J. 5:1921–1927); pZipNeo SV (Cepko et al., 1984, Cell 37:1053–1062); pSRα (DNAX, Palo Alto, Calif.); pBK-CMV (Stratagene, La Jolla, Calif.); pCDNA3 (In Vitrogen, Carlsbad, Calif.); and pCDNA1 (In Vitrogen, Carlsbad, Calif.). Where the KDELr inhibitor protein is oligomeric, oligomers may be formed in vivo or in vitro. An example of conditions which would produce such oligomers in vitro would be a room temperature solution including oxidized and reduced glutathione at concentrations of 10 mM and 2 mM, respectively (Efimov et al., 1994, FEBS Let. 341:54–58).

Any of the KDELr inhibitor proteins described above may be introduced into a cell, wherein the cell is synthesizing, has synthesized, or will synthesize a protein which would tend to bind to a KDEL receptor and hence be returned to the endoplasmic reticulum (hereafter referred to as an "ER protein"), where it is desired that the KDEL receptor inhibitory protein promote the secretion of the ER protein. A KDELr inhibitor protein may be introduced into the cell by any means known in the art, including the introduction of a gene encoding the KDELr inhibitor protein or microvesicles comprising KDELr inhibitor protein.

Where the KDELr inhibitor protein is genetically introduced, a nucleic acid encoding said KDELr inhibitor protein should also encode a signal sequence linked to said protein which targets the KDELr inhibitor protein to the endoplasmic reticulum. Nonlimiting examples of signal sequences which may be used include the mouse BiP signal peptide shown in FIGS. 1–5, the adenovirus E3/19kd signal peptide (Anderson et al., 1991, J. Exp. Med. 174:489–492) as shown in FIGS. 6–9, the human pre-prolactin signal peptide or the human pre-proinsulin signal peptide.

Where the KDELr inhibitor itself is to be introduced into a cell, it may be linked to one or more sugar residue to facilitate its uptake into endosomes, for example, via the insulin receptor (Krupp and Lane, 1982, J. Biol. Chem. 257:1372–1377), the mannose 6 phosphate receptor or the asialoglycoprotein receptor (Berg et al., 1982, Exp. Cell Res. 148:319–330) and Wu, 1988, Biochem. 27:887–892; Plank et al., 1992, Bioconjugate Chem. 3:533–539), or linked to another biological molecule, such as folate (for uptake via the folate receptor; Wang et al., 1995, Proc. Natl. Acad. Sc. U.S.A. 92:3318), insulin (for uptake via the insulin receptor; Huckett et al., 1990, Biochem. Pharmacol. 40:253) or transferrin (for uptake via the transferrin receptor; Kuhn et al., 1984, Cell 37:95–103; McClelland et al., 1984, Cell 39:267–274; Morgan et al., 1978, Blood 52:1219–1228; Karin and Mintz, 1981, J. Biol. Chem. 256:3245–3252; Octave et al., 1983, Trends Biochem. Sci. ("TIBS") 8:217–220; Newman et al., 1982, TIBS 7:397–400; Zenke et al., 1990, Proc. Natl. Acad. Sci. U.S.A. 87:3655). As a nonlimiting specific example, FIG. 10 depicts a KDEL inhibitor protein comprising an N-linked glycosylation site. The consensus site for N-glycosylation is NXT or NXS. The sequence NST, comprised in the protein depicted in FIG. 10, is used as an optimized sequence for glycosylation in a context related to KDEL peptide (Misenbock and Rothman, 1995, J. Cell Biol. 129:309–319; see also Kim et al., 1998, Proc. Natl. Acad. Sci. U.S.A. 95:2997–3002). The molecule depicted in FIG. 10 also comprises a myc-tag sequence (Glu-Gln-Lys-Leu-Ile-Ser-Glu-Glu-Asp-Leu; SEQ ID NO: 36), which may be used as a marker for localization of the protein using, for example, monoclonal antibody 9E 10.

Where nucleic acid encoding the KDELr inhibitor protein is to be introduced into a cell, it may be comprised in any suitable vector, including, but not limited to, herpes simplex viral based vectors such as pHSV1 (Geller et al., 1990, Proc. Natl. Acad. Sci. U.S.A. 87:8950–8954); retroviral vectors such as MFG (Jaffee et al., 1993, Cancer Res. 53:2221–2226), and in particular Moloney retroviral vectors such as LN, LNSX, LNCX, and LXSN (Miller and Rosman, 1989, Biotechniques 7:980–989); vaccinia viral vectors such as MVA (Sutter and Moss, 1992, Proc. Natl. Acad. Sci. U.S.A. 89:10847–10851); adenovirus vectors such as pJM17 (Ali et al., 1994, Gene Therapy 1:367–384; Berker, 1988, Biotechniques 6:616–624; Wand and Finer, 1996, Nature Medicine 2:714–716); adeno-associated virus vectors such as AAV/neo (Mura-Cacho et al., 1992, J. Immunother. 11:231–237), and naked DNA vectors (International Application Publication No. WO 94/21797, by Merck et al.;International Application Publication No. WO 90/11092, by Vical et al.; U.S. Pat. No. 5,589,466; U.S. Pat. No. 5,580,859).

A KDELr inhibitor protein of the invention may be further modified, for example, to improve its half-life or activity or to alter its immunogenicity (i.e., increase or decrease the subtype of immunity elicited). In particular embodiments of the invention, a KDELr inhibitor protein of the invention may be conjugated to a second molecule, such as polyethylene glycol, or to an antigenic peptide. As a specific nonlimiting example of the latter, an antigenic peptide may be linked to one or more iterations of the N-linked glycosylation tripeptide sequence Asn-X-Thr comprised in a KDELr inhibitor protein. Expression of such a KDELr inhibitor protein/antigenic peptide complex in a lectin resistant cell line, such as 15B Chinese Hamster Ovary (CHO) cells or 1021 CHO cells, may be used to produce a mannosylated or sialylated KDELr inhibitor protein which may saturate endogenous KDEL receptors and be secreted into the surrounding culture medium. Secreted and non-secreted forms of this protein may be comprised in a vaccine formulation; by virtue of its mannosylation or sialylation, the KDELr inhibitor protein would be favored for uptake via incorporation into endosomes (Engering et al., 1997, Eur. J. Immunol. 27:2417–2425). In further embodiments of the invention, a KDELr inhibitor protein may be linked to another protein molecule as a fusion peptide or protein. As one nonlimiting example, nucleic acid encoding a KDELr inhibitor protein may be cloned at the 5' or 3' end of another molecule, using, e.g., the BamHI or KpnI restriction sites depicted in FIGURE IA. As another nonlimiting example, a targeting sequence may be incorporated into the amino terminal region of a KDELr inhibitor protein downstream from a cleavably removed sequence; suitable targeting sequences would include the $\alpha_v$ integrin binding motif Arg-Gly-Asp (RGD) or Cys-Asp-Cys-Arg-Gly-Asp-Cys-Phe-Cys (SEQ ID NO:33; termed "RGD-4C"; Arap et al., 1998, Science 279:377–380). Alternatively, such a motif could be placed at a more 3' site preceding KDEL (SEQ ID NO:37).

In a first nonlimiting example of the invention, a KDELr inhibitor protein may be formed by creating a pentamer of monomeric units, wherein each monomer comprises a COMP pentamerization domain and the protein has, at its C terminus, the amino acid sequence KDEL (SEQ ID NO:37). FIG. 1A depicts a nucleic acid molecule encoding one such monomeric unit, wherein a cleavable signal peptide is attached, via a linker sequence, to the pentamerization domain of rat COMP, which is in turn attached, via a linker derived from camel immunoglobulin IgG, to a C-terminal KDEL sequence (SEQ ID NO:37). This construct may be incorporated into an expression vector, such as, but not limited to, pCDNA3, and used to produce monomers which under normal expression conditions assemble to form the pentameric KDELr inhibitor protein.

In a second nonlimiting example of the invention, a KDELr inhibitor protein may be formed by creating a trimer of monomeric units, wherein each monomer comprises a mouse thrombospondin 3 (TSP3) trimerization domain and the protein has, at its C terminus, the amino acid sequence KDEL. FIGS. 3A and 4A depict nucleic acid molecules encoding one such monomeric unit, wherein a signal peptide is attached, via a linker sequence, to the trimerization domain of mouse TSP3, which is in turn attached, via a linker derived from camel immunoglobulin IgG, to a C-terminal KDEL sequence. This construct may be incorporated into an expression vector, such as, but not limited to, pCDNA3 and used to produce monomers which under normal expressison conditions assemble to form the trimeric KDELr inhibitor protein.

In a third nonlimiting example of the invention, a KDELr inhibitor protein may be formed by creating a pentamer of monomeric units, wherein each monomer comprises a human COMP pentamerization domain and the protein has, at its C terminus, the amino acid sequence KDEL (SEQ ID NO:37). FIG. 6A depicts a nucleic acid molecule encoding one such monomeric unit, wherein a signal peptide is attached, via a linker sequence, to the pentamerization domain of human COMP, which is in turn attached, via a linker derived from camel immunoglobulin IgG, to a C-terminal KDEL sequence (SEQ ID NO:37). This construct may be incorporated into an expression vector, such as, but not limited to, pCDNA3 and used to produce monomers which under normal expressison conditions assemble to form the pentameric KDELr inhibitor protein.

In further related nonlimiting examples of the invention, KDELr inhibitor proteins may be prepared using constructs depicted in FIG. 7A (using the human phospholamban oligomerization domain to produce pentamers); FIG. 8A (using the human thrombospondin 3 oligomerization domain to produce trimers); FIG. 9A (using the human thrombospondin 4 oligomerization domain to produce trimers); and FIG. 5A (using the Xenopus thrombospondin 4 oligomerization domain to produce trimers).

5.2. USES OF KDEL RECEPTOR INHIBITORS

The present invention provides for a number of therapeutic and commercial uses for KDEL receptor inhibitors.

The term "KDEL receptor inhibitor", as used herein, includes but is not limited to the KDELr inhibitor proteins described in the preceding section. Non-protein molecules as well as molecules comprising a majority of non-protein elements are also encompassed by the scope of this term. Such inhibitors share the common property of inhibiting the ability of the KDEL receptor to return proteins containing a ligand sequence for the KDEL receptor to the endoplasmic reticulum. For example, KDEL receptor inhibitors may compete with the ligand sequence for binding with the KDEL receptor (e.g., the oligomeric protein comprising a plurality of such ligand sequences described above), but the term includes inhibitors which act by other mechanisms as well (for example, agents which increase the ability of the KDEL receptor to release its bound proteins).

To identify KDEL receptor inhibitors, the ability of a putative inhibitor compound may be tested in vivo for its ability to promote the secretion of proteins which normally tend to bind to the KDEL receptor and be retained in the cell, particularly in the endoplasmic reticulum. This may be accomplished by quantitating the rate and amount of release of one or more such proteins from a cell, tissue, or cell culture in the presence and absence of putative inhibitor and/or at various concentrations of putative inhibitor. As one nonlimiting example, the distribution of a detectably labeled protein may be followed, as was done with a protein marked with an 11 amino acid sequence derived from the human c-myc gene in Munro and Pelham, 1987, Cell 48:899–907.

Alternatively, KDEL receptor inhibitors may be identified by testing the ability of putative inhibitors to bind to a KDEL receptor in vitro. In nonlimiting embodiments, the ability of such putative KDEL inhibitors to compete with a known KDEL receptor ligand or a known KDEL receptor inhibitor for binding to a KDEL receptor may be tested. As a specific, nonlimiting example, the ability of a putative inhibitor to compete with a KDELr inhibitor protein (as described in the preceding section) for binding to a KDEL receptor may be determined. Such in vitro testing may desirably be performed under conditions which are similar to those found within the cell, for example, see Wilson et al., 1993, J. Biol. Chem. 268:7465–7468).Suitable sources for KDEL receptor include Golgi membrane prepared from rat liver or COS cells expressing the erd2 receptor. Putative inhibitors which appear to function as KDEL receptor inhibitors in vitro may then be further evaluated for their ability to inhibit KDEL receptor function in vivo.

As set forth above, KDEL receptor inhibitors may be used to increase the secretion of a protein which would otherwise tend to be retained in a cell by virtue of the action of the KDEL receptor, when secretion of such protein is desirable. Situations where increased secretion of a protein would be advantageous would include (i) where genetic engineering has introduced a gene encoding a protein, hereafter referred to as an "exogenous protein", into a cell, and it desirable that the exogenous protein is secreted (e.g., as a specific nonlimiting example, where the exogenous protein is a heat shock protein); and (ii) where it is desirable to increase the secretion of a protein which has not been introduced by genetic engineering but which occurs in the cell either normally or as a result of a disease process such as infection or malignancy (e.g., a native heat shock protein or a viral protein), hereafter referred to as an "endogenous protein".

Accordingly, the present invention provides for a method of increasing the secretion of an exogenous or endogenous protein by a cell, wherein the protein comprises a ligand sequence which binds to a KDEL receptor, comprising exposing the cell to a KDEL receptor inhibitor at a concentration which increases the secretion of the protein from the cell relative to the secretion of the protein in the absence of the KDEL receptor inhibitor.

In one series of nonlimiting embodiments, where it is desirable that an exogenous protein is secreted, a nucleic acid encoding both the exogenous protein as well as a KDELr inhibitor protein (as part of the same, or distinct, nucleic acid constructs), may be introduced into a cell. According to this specific embodiment, the introduction of two distinct constructs, one encoding the desired protein and the other encoding the KDELr inhibitor protein, may be used to more accurately target the secretion of the desired protein to a particular subset of cells or tissues (that is to say, the introduced protein will be selectively secreted when both constructs are present). In related embodiments, nucleic acid encoding the desired protein and/or the KDELr inhibitor protein may be placed under the control of tissue specific or inducible promoter/enhancer elements.

In a second series of nonlimiting embodiments, where it is desirable that an endogenous protein is secreted, a KDEL receptor inhibitor, for example a KDELr inhibitor protein, may be introduced into a cell of a subject in need of such treatment, either by administration of the KDEL receptor inhibitor itself or via a nucleic acid encoding a KDELr inhibitor protein. As an example of such embodiments, heat shock proteins are known to associate with antigenic peptides to form complexes which induce an immune response to the bound peptides, and, since certain heat shock proteins tend to be selectively retained in the endoplasmic reticulum via the KDEL receptor system (including BiP and gp96), the present invention may be used to promote secretion of the antigenic heat shock protein complexes and thereby to induce or increase an immune response to a target antigen.

The target antigen may be associated with an infectious disease or a cancer, including antigens associated with neoplasia such as sarcoma, lymphoma, leukemia, melanoma, carcinoma of the breast, carcinoma of the prostate, ovarian carcinoma, carcinoma of the cervix, uterine carcinoma, colon carcinoma, carcinoma of the lung, glioblastoma, and astrocytoma, antigens associated with defective tumor suppressor genes such as p53; antigens associated with oncogenes such as ras, src, erbB, fos, abl, and myc; antigens associated with infectious diseases caused by a bacterium, virus, protozoan, mycoplasma, fungus, yeast, parasite or prion; and antigens associated with an allergy or autoimmune disease. Examples of sources of antigens associated with infectious disease include, but are not limited to, a human papilloma virus (see below), a herpes virus such as herpes simplex or herpes zoster, a retrovirus such as human immunodeficiency virus 1 or 2, a hepatitis virus, an influenza virus, a rhinovirus, a respiratory syncytial virus, a cytomegalovirus, an adenovirus, *Mycoplasma pneumoniae*, a bacterium of the genus Salmonella, Staphylococcus, Streptococcus, Enterococcus, Clostridium, Escherichia, Klebsiella, Vibrio, or Mycobacterium, and a protozoan such as an amoeba, a malarial parasite, and Trypanosoma cruzi.

Specific, nonlimiting examples of human papilloma virus antigenic peptides which may serve as target antigens according to the invention are:

Leu-Leu-Leu-Gly-Thr-Leu-Asn-Ile-Val (SEQ ID NO: 8);

Leu-Leu-Met-Gly-Thr-Leu-Gly-Ile-Val (SEQ ID NO: 9);

Thr-Leu-Gln-Asp-Ile-Val-Leu-His-Leu (SEQ ID NO: 10);

Gly-Leu-His-Cys-Tyr-Glu-Gln-Leu-Val (SEQ ID NO: 11); and

Pro-Leu-Lys-Gln-His-Phe-Gln-Ile-Val (SEQ ID NO: 12).

Accordingly, the present invention relates to a method for promoting the release of a heat shock protein/antigenic peptide complex from a cell, where the heat shock protein contains a ligand sequence which binds to a KDEL receptor, comprising exposing the cell to a KDEL receptor inhibitor at a concentration which increases the secretion of the complex from the cell relative to the secretion of the complex in the absence of the KDEL receptor inhibitor. Where the KDEL receptor inhibitor is a protein, it may be administered as a protein or as a nucleic acid encoding said KDELr inhibitor protein (using "genetic vaccination techniques" including, but not limited to, techniques whereby "naked DNA" encoding the KDELr inhibitor protein is administered to a subject).

In related embodiments, the present invention further provides for a method of inducing or increasing an immune response to a target antigen, comprising administering an effective amount of a KDEL receptor inhibitor, where the target antigen forms a complex with a heat shock protein and the heat shock protein contains a ligand sequence which binds to a KDEL receptor. The target antigen may be an endogenous antigen or may be introduced, either by an encoding nucleic acid or in peptide form. Similarly, the heat shock protein may be an endogenous heat shock protein or may be introduced by gene therapy techniques.

In a specific, nonlimiting embodiment, the present invention envisions the use of a KDEL receptor inhibitor which may be used to boost immunity in a subject in need of such treatment; examples would include a subject at risk of developing a cancer in view of a genetic predisposition or carcinogen exposure, or a subject at risk for developing infection in view of a compromised immune system and/or pathogen exposure. Under circumstances where the antigen has not yet been identified, immunity may be induced toward endogenous antigen(s). Where target antigen(s) is (are) known, a KDEL receptor inhibitor may be administered in conjunction with a target antigen, which may be comprised in a vaccine administered by any standard route (e.g., subcutaneously, intramuscularly, intranasally, etc.). An orally administered KDEL receptor inhibitor may be particularly advantageous.

Because systemic administration of a KDEL receptor inhibitor may be expected to transiently induce widespread release of proteins normally retained in the endoplasmic reticulum, it may be desirable to administer a KDEL receptor inhibitor having a short half-life at intervals which minimize any toxic effects, for example, but not by way of limitation, one dose every two weeks for a month. Alternatively, a KDEL receptor inhibitor may be locally administered to a site containing endogenous antigen (for example, a malignant tumor or infected tissue) or a site containing exogenous antigen (for example, but not by way of limitation, a site wherein nucleic acid encoding target antigen has been administered).

The present invention further provides for a non-human transgenic animal carrying, as a transgene, in all or a subpopulation of the cells of the animal, nucleic acid encoding a exogenous KDELr inhibitor protein (as distinct from KDEL (SEQ ID NO:37)-bearing proteins normally present in the animal), operably linked to a promoter sequence. In preferred nonlimiting embodiments of the invention,the promoter is an inducible promoter. Such a transgenic animal may be used to study the effects of promoting the secretion of an endogenous or exogenously introduced protein of interest.

Where a protein comprising a ligand sequence for a KDEL receptor is being commercially produced, a KDEL receptor inhibitor of the invention may be used to promote secretion of the protein and therefore facilitate its manufacture.

Accordingly, the present invention provides for compositions comprising a KDEL receptor inhibitor, or a nucleic acid encoding a KDEL receptor inhibitor, in a suitable pharmaceutical carrier. Such compositions may further comprise a target antigen or a nucleic acid encoding a target antigen or a precursor of a target antigen which is processed in a cell to yield a target antigen, a nucleic acid encoding a heat shock protein, a cytokine which promotes the activity of the immune system, such as interleukin 2 and/or alpha interferon, and/or an agent which facilitates protein secretion, such as monensin.

For illustrative purposes only, specific, nonlimiting embodiments of the invention may be practiced as follows.
1. Expression And Purification Of Recombinant rCOMP-KDELr Inhibitor Proteins.

Rat COMP-KDELr inhibitor protein encoded by a pet 11-derived plasmid prepared using the construct depicted in FIG. 1A, under the control of the T7 promoter, may be expressed in *E. coli* BL21 (DE3) cells, according to the method described in Efimov et al., 1994, FEBS Letts. 341:54–58. Vector-containing bacteria may be cultured in shaker flasks at 37° C. to an $OD_{600}$ of approximately 0.5–0.6, and then 1.0 mM isopropyl β-D-thiogalactoside may be added per liter of culture to induce protein synthesis. After further incubation for about four hours at 30° C., bacterial cells may be harvested by centrifugation at 8000×g for 15 minutes at 4° C. Bacterial pellets may then be resuspended in 20 ml TE buffer (20 mM Tris-HCl, pH 8.0, 1 mM EDTA) containing 0.1 mg/ml lysozyme, and then incubated at 25° C. or room temperature for about 30 minutes. Alternatively, bacterial cells may be lysed using a cell disruptor such as Emulsiflex C-5 (Avestin, Ontario, Canada). The resulting cell lysate may be incubated with 0.1 mg/ml DNAase I for 15 minutes at 25° C. (room temperature) and then centrifuged at 23,000×g at 4° C. for fifteen minutes to remove insoluble material. These conditions may also be used for subsequent centrifugations. Two milliliters of 30 percent w/v streptomycin sulfate solution may be mixed with the resulting supernatant and the mixture may be incubated on ice for 15 minutes. The resulting precipitate may be removed by centrifugation and ammonium sulfate may be added to the supernatant to about 36 percent saturation, and the solution may be incubated on ice for about 15 minutes to produce an ammonium sulfate/protein precipitate. The ammonium sulfate/protein precipitate may then be collected by centrifugation as set forth above. The pellet obtained by centrifugation may be resuspended in 2 ml TE buffer and applied to a 10 ml hydroxylapatite column (BioRad, DNA grade), pre-equilibrated with 10 mM sodium phosphate, pH 7.6. The column may be washed with the pre-equilibration buffer having an increasing phosphate gradient, and the flow-through protein fraction, which would be expected to contain mainly the recombinant rCOMP-KDELr inhibitor protein, may be collected. Analogous methods may be used to purify KDELr inhibitor protein expressed in 15B CHO cells or insect cells.

Oligomerization of the recombinantly expressed protein may be achieved as follows, using a method as described in Efimov et al., 1994, FEBS Letts. 341:54–58. Purified KDELr inhibitor protein may be substantially (preferably completely) reduced by incubation with a 100-fold molar excess of dithiothreitol (DTT) for about 30 minutes at 37° C., followed by precipitation with 50 percent ammonium sulfate, followed by centrifugation as set forth above. The resulting pellet may be resuspended in 0.2 M Tris-HCl, pH 8.8, 0.2 M NaCl, 1 mM EDTA to a final protein concentration of 1.5 mg/mL. The protein may be oxidized at room temperature by addition of oxidized and reduced glutathione to final concentrations of 10 mM and 2 mM respectively over a period of about 14 hours. The oxidized protein may then be separated from glutathione by HPLC or dialysis. The correctly folded pentamer may also be purified by reverse phase chromatography on a C4 column.

The KDELr inhibitor protein may also be oligomerized by the method described in Jaenicke and Rudolph, 1989, in Creighton et al., *Protein Structure: a practical approach*. IRL Press Oxford, pp. 208–209, wherein the protein may be first reduced by incubation for 2 hours in 0.1 M DTT, 6 M guanidine hydrochloride, 1 mM EDTA and 0.1 M Tris-HCl, pH 8.3, followed by acidification and dialysis overnight at 4° C. against 0.01 M HCl, and then refolded for about 16 hours at 16° C. in an oxido-shuffling system containing 0.3 mM cysteine and 3 mM cysteine, 1 mM EDTA and 0.1 M Tris-HCL, pH 8.3. The protein may subsequently be purified by HPLC, lyophilized and stored at 4° C.
2. Testing The Ability of KDEL Receptor Inhibitor To Bind To KDEL Receptor.

The ability of KDEL receptor inhibitors of the invention to bind to KDEL receptor may be tested in vitro using alkali-washed Golgi membranes. Such membranes may be prepared from livers of freshly sacrificed rats using the methods described by Tabas and Kornfeld, 1979, J. Biol. Chem. 254:11655–11663, or from cultured cells expressing erd 2 receptors in their Golgi membranes. For example, harvested liver or cultured cells may be dounced and used to prepare a 1500×g postnuclear supernatant, which may then be spun at 100,000×g to recover a crude membrane fraction. The resulting crude membranes may then be washed with 100 mM $Na_2CO_3$ at 4° C., pelleted by centrifugation at 100,000×g, and then resuspended in 10 mM HEPES-KOH, pH 7.5 to produce alkali-washed Golgi membrane.

The alkali-washed Golgi membrane may then be used in a binding assay as described by Wilson et al., 1993, J. Biol. Chem. 268:7465–7468 to determine whether a putative KDEL receptor inhibitor binds to the erd 2 (KDEL) receptor. The ability of a putative KDEL receptor inhibitor to bind to the erd 2 receptor may be determined by measuring the ability of the inhibitor to compete with a detectably labeled peptide which binds the erd 2 receptor, such as Tyr-Thr-Ser-Glu-Lys-Asp-Glu-Leu (SEQ ID NO:3 1) or Leu-Asn-Tyr-Phe-Asp-Asp-Glu-Leu (SEQ ID NO:32) for receptor binding. Such peptides may, for example, be radioiodinated by incubation with 1 mCi of [$^{125}I$] iodide for one minute in the presence of 2.4 mg/ml of chloramine T (BDH Chemicals, Ltd.) quenched and the iodinated peptides may be separated on a Sephadex G-10 column (Pharmacia) as described in Harlow and Lane, 1988, in *Antibodies: a laboratory manual*, Cold Spring Harbor Press, Cold Spring Harbor, N.Y. The binding assay buffer may contain 20 mM NaCl, 250 mg/ml bovine serum albumin, 50 mM sodium or potassium cacodylate or citrate, pH 5.0–5.5, MES (2-[N-morpholino]ethane sulfonic acid) or a mixture of succinate and PIPES (piperazine-N,N'-bis[2-ethanesulfonic acid) at the same molarity. Putative KDEL receptor inhibitor at various concentrations, total membrane protein (for example 0.5–1.0 µg), radiolabeled peptide (for example, 0.1–0.5 ng peptide having 1×10$^5$ cpm) and alkali-washed Golgi membrane at 2–4 percent w/v may be incubated in (e.g., 25 µl) binding assay buffer at 4° C. for about 20 minutes, and then centrifuged in a microfuge (at about 15,800×g) at 4° C. for 5 minutes, and the amount of labeled peptide present in the pellet may be determined. An observed decrease in bound labeled peptide with increasing concentrations of putative KDEL receptor inhibitor indicates that the putative KDEL receptor inhibitor is binding to the erd 2 receptor.

3. Introduction of rCOMP/KDELr Inhibitor Protein Into Tumor Cells.

A 375 base pair Hind III—Xho I fragment of a partial gene construct encoding a cleavable signal peptide (such as the signal peptide from the murine heat shock protein BiP) at the 5' end linked to the rat COMP pentamerization domain followed by the camel IgG domain (see FIG. 1A) may be synthesized (for example, by a commercial entity such as Oligos, Etc., Inc., Oregon). The resulting fragment may be cloned into a mammalian expression vector such as pCDNA3 by standard techniques (see, for example, Sambrook et al., 1990, *Molecular Cloning: A Laboratory Manual* (Cold Spring Harbor Lab. Press, Plainview, N.Y.), using the Hind III-Xho I restriction sites and transformed into TOP 10F' competent cells (which may be obtained from In Vitrogen, Inc.). The sequences of the resulting plasmid, rCOMP/pCDNA3 may be verified by dideoxy sequencing (Sanger et al., 1977, Proc. Natl. Acad. Sci. U.S.A. 74:5463–5467) using Sequenase 2.0 (United States Biochemical).

A 72 base pair double-stranded KDEL (SEQ ID NO:37)-containing oligonucleotide may then be annealed at the 3' end of rCOMP-pCDNA3 using the Kpn I-Eco RI restriction endonuclease site (see FIG. 1A) to generate rCOMP-KDELr inhibitor/pCDNA3. This construct may then be verified by dideoxynucleotide sequencing.

The construct rCOMP-KDELr inhibitor/pCDNA3 may then be expressed, for example, in a tumor cell line such as CMS-5. CMS-5 is a methylcholanthrene-induced fibrosarcoma of BALB/c origin, shown to be devoid of viral antigens (DeLeo et al., 1977, J. Exp. Med. 146:720–734). CMS-5 cells may be adapted to culture and grown in DMEM medium (Gibco Life Technologies, Inc.) supplemented with 10% fetal calf serum (FCS). Transfection may be carried out using lipofectamine, according to the manufacturer's instructions (Gibco-BRL Life Technologies). Briefly, 2 µg of cDNA and 6 µL of lipofectamine may be diluted separately into 100 µL serum-free medium (OPTI-MEM® I Reduced Serum medium, Gibco-BRL Life Technologies). The two solutions may then be mixed and incubated at room temperature for about 45 minutes to allow the formation of DNA-liposome complexes. 800 µL of OPTI-MEM® may be added to the resulting complexes, mixed, and overlaid onto rinsed cells. After an approximately six hour incubation period at 37° C., one milliliter of growth medium containing 20% FCS may be added. Fresh medium may be added to the cells 24 hours post-transfection. Stable clones may be selected by adding 800 µg/ml geneticin (Gibco-BRL Life Technologies) to the cells 72 hours later. The selection medium may be changed about every three days. Colonies of stably transfected cells may be screened for expression of rCOMP/KDELr inhibitor proteins using antiserum raised against bovine COMP (Hedbom et al., 1992, J. Biol. Chem. 264:6898–6905). This antibody has been shown to stain rat COMP under both nonreducing as well as reducing conditions (Morgelin et al., 1992, J. Biol. Chem. 267:6137–6141).

Stably transfected tumor cells produced in this manner may be utilized in a number of ways. For example, they may be used to determine whether increased secretion of a particular protein, normally retained by the KDEL receptor, may effect the tumorigenicity of the cells. In one specific nonlimiting example, they may be used to determine whether the secretion of an endogenous heat shock protein is increased and whether the increased secretion of endogenous protein decreases the tumorigenicity of the cells (e.g., stably transfected CMS-5 cells described above may be inoculated into CB6F-1I/J mice). In another specific nonlimiting example, stably transfected tumor cells may further be transfected with nucleic acid encoding an exogenous protein, and it may be determined whether increased secretion of the exogenous protein by the tumor cells decreases their tumorigenicity.

Various references are cited herein, the contents of which are hereby incorporated by reference in their entireties.

What is claimed is:

1. An oligomeric KDEL receptor inhibitor protein comprising a trimer of protein subunits, wherein each subunit comprises an oligomerization domain and has, at its carboxy terminus, a region which binds to a KDEL receptor.

2. The KDEL receptor inhibitor protein of claim 1, wherein the region which binds to a KDEL receptor has the amino acid sequence Lys-Asp-Glu-Leu (SEQ ID NO:37).

3. An oligomeric KDEL receptor inhibitor protein comprising a plurality of protein subunits, wherein each subunit comprises an oligomerization domain and has, at its carboxy terminus, a region which binds to a KDEL receptor, wherein the oligomerization domain is a pentamerization domain.

4. The KDEL receptor inhibitor protein of claim 3, wherein the oligomerization domain is a pentamerization domain and wherein the region which binds to a KDEL receptor has the amino acid sequence Lys-Asp-Glu-Leu (SEQ ID NO:37).

5. The KDEL receptor inhibitor protein of claim 3, wherein the pentamerization domain is derived from a cartilage oligomeric matrix protein.

6. The KDEL receptor inhibitor protein of claim 5, wherein the pentamerization domain has the amino acid sequence Gly-Asp-Leu-Ala-Pro-Gln-Met-Leu-Arg-Glu-Leu-Gln-Glu—Thr-Asn-Ala-Ala-Leu-Gln-Asp-Val-Arg-Glu-Leu-Leu-Arg-Gln-Gln-Val-Lys-Glu-Ile-Thr-Phe—Leu-Lys-Asn-Thr-Val-Met-Glu-CysAsp-Ala-Cys-Gly (SEQ ID NO: 1).

7. The KDEL receptor inhibitor protein of claim 5, wherein the pentamerization domain has the amino acid sequence Ser-Asp-Leu-Gly-Pro-Gln-Met-Leu-Arg-Glu-Leu-Gln—Glu-Thr-Asn-Ala-Ala-Leu-Gln-Asp-Val-Arg-Asp-Trp-Leu-Arg-Gln-Gln-Val-Arg-Glu-Ile-Thr—Phe-Leu-Lys-Asn-Thr-Val-Met-Glu-Cys-Asp-Ala-Cys-Gly (SEQ ID NO:2).

8. An oligomeric KDEL receptor inhibitor protein comprising a plurality of protein subunits, wherein each subunit comprises an oligomerization domain and has, at its carboxy terminus, a region which binds to a KDEL receptor, wherein the oligomerization domain is derived from a thrombospondin protein.

9. The KDEL receptor inhibitor protein of claim 8, wherein the oligomerization domain has the amino acid sequence Gly-Glu-Gln-Thr-Lys-Ala-Leu-Val-Thr-Gln-Leu-Thr-Leu—Phe-Asn-Gln-Ile-Leu-Val-Glu-Leu-Arg-Asp-Asp-Ile-Arg-Asp-Gln-Val-Lys-Glu-Met-Ser-Leu—Ile-Arg-Asn-Thr-Ile-Met-Glu-Cys-Gln-Val-Cys-Gly (SEQ ID NO:3).

10. The KDEL receptor inhibitor protein of claim 8, wherein the oligomerization domain has the amino acid sequence Gly-Glu-Gln-Thr-Lys-Ala-Leu-Val-Thr-Gln-Leu-Thr-Leu—Phe-Asn-Gln-Ile-Leu-Val-Glu-Leu-Arg-Asp-Asp-Ile-Arg-Asp-Gln-Val-Lys-Glu-Met-Ser-Leu— Ile-Arg-Asn-Thr-Ile-Met-Glu-Cys-Gln-Val-Cys-Gly (SEQ ID NO:4).

11. The KDEL receptor inhibitor protein of claim 8, wherein the oligomerization domain has the amino acid sequence Gly-Asp-Phe-Asn-Arg-Gln-Phe-Leu-Gly-Gln-Met-Thr—Gln-Leu-Asn-Gln-Leu-Leu-Gly-Glu-Val-Lys-Asp-Leu-Leu-Arg-Gln-Gln-Val-Lys-Glu-Thr-Ser—Phe-Leu-Arg-Asn-Thr-Ile-Ala-Glu-Cys-Gln-Ala-Cys-Gly (SEQ ID NO:5).

12. The KDEL receptor inhibitor protein of claim 8, wherein the oligomerization domain has the amino acid sequence Gly-Asp-Val-Ser-Arg-Gln-Leu-Ile-Gly-Gln-Ile-Thr-Gln—Met-Asn-Gln-Met-Leu-Gly-Glu-Leu-Arg-Asp-Val-Met-Arg-Gln-Gln-Val-Lys-Glu-Thr-Met—Phe-Leu-Arg-Asn-Thr-Ile-Ala-Glu-Cys-Gln-Ala-Cys-Gly (SEQ ID NO:6).

13. An oligomeric KDEL receptor inhibitor protein comprising a plurality of protein subunits, wherein each subunit comprises an oligomerization domain and has, at its carboxy terminus, a region which binds to a KDEL receptor, wherein the oligomerization domain has the amino acid sequence Gln-Lys-Leu-Gln-Asn-Leu-Phe-Ile-Asn-Phe-Cys-Leu-Ile-Leu-Ile-Cys-Leu-Leu-Leu-Ile-Cys-Ile-Ile-Val-Met-Leu-Leu (SEQ ID NO:7).

* * * * *

SEQUENCE LISTING

<160> NUMBER OF SEQ ID NOS: 42

<210> SEQ ID NO 1
<211> LENGTH: 46

```
<212> TYPE: PRT
<213> ORGANISM: Ratus ratus

<400> SEQUENCE: 1

Gly Asp Leu Ala Pro Gln Met Leu Arg Glu Leu Gln Glu Thr Asn Ala
 1               5                  10                  15

Ala Leu Gln Asp Val Arg Glu Leu Leu Arg Gln Gln Val Lys Glu Ile
             20                  25                  30

Thr Phe Leu Lys Asn Thr Val Met Glu Cys Asp Ala Cys Gly
         35                  40                  45

<210> SEQ ID NO 2
<211> LENGTH: 46
<212> TYPE: PRT
<213> ORGANISM: Homo sapiens

<400> SEQUENCE: 2

Ser Asp Leu Gly Pro Gln Met Leu Arg Glu Leu Gln Glu Thr Asn Ala
 1               5                  10                  15

Ala Leu Gln Asp Val Arg Asp Trp Leu Arg Gln Gln Val Arg Glu Ile
             20                  25                  30

Thr Phe Leu Lys Asn Thr Val Met Glu Cys Asp Ala Cys Gly
         35                  40                  45

<210> SEQ ID NO 3
<211> LENGTH: 46
<212> TYPE: PRT
<213> ORGANISM: Mus musculus

<400> SEQUENCE: 3

Gly Glu Gln Thr Lys Ala Leu Val Thr Gln Leu Thr Leu Phe Asn Gln
 1               5                  10                  15

Ile Leu Val Glu Leu Arg Asp Asp Ile Arg Asp Gln Val Lys Glu Met
             20                  25                  30

Ser Leu Ile Arg Asn Thr Ile Met Glu Cys Gln Val Cys Gly
         35                  40                  45

<210> SEQ ID NO 4
<211> LENGTH: 46
<212> TYPE: PRT
<213> ORGANISM: Homo sapiens

<400> SEQUENCE: 4

Gly Glu Gln Thr Lys Ala Leu Val Thr Gln Leu Thr Leu Phe Asn Gln
 1               5                  10                  15

Ile Leu Val Glu Leu Arg Asp Asp Ile Arg Asp Gln Val Lys Glu Met
             20                  25                  30

Ser Leu Ile Arg Asn Thr Ile Met Glu Cys Gln Val Cys Gly
         35                  40                  45

<210> SEQ ID NO 5
<211> LENGTH: 46
<212> TYPE: PRT
<213> ORGANISM: Homo sapiens

<400> SEQUENCE: 5

Gly Asp Phe Asn Arg Gln Phe Leu Gly Gln Met Thr Gln Leu Asn Gln
 1               5                  10                  15

Leu Leu Gly Glu Val Lys Asp Leu Leu Arg Gln Gln Val Lys Glu Thr
             20                  25                  30
```

```
Ser Phe Leu Arg Asn Thr Ile Ala Glu Cys Gln Ala Cys Gly
        35                  40                  45
```

<210> SEQ ID NO 6
<211> LENGTH: 46
<212> TYPE: PRT
<213> ORGANISM: Xenopus laevis

<400> SEQUENCE: 6

```
Gly Asp Val Ser Arg Gln Leu Ile Gly Gln Ile Thr Gln Met Asn Gln
 1               5                  10                  15

Met Leu Gly Glu Leu Arg Asp Val Met Arg Gln Gln Val Lys Glu Thr
            20                  25                  30

Met Phe Leu Arg Asn Thr Ile Ala Glu Cys Gln Ala Cys Gly
        35                  40                  45
```

<210> SEQ ID NO 7
<211> LENGTH: 27
<212> TYPE: PRT
<213> ORGANISM: Homo sapiens

<400> SEQUENCE: 7

```
Gln Lys Leu Gln Asn Leu Phe Ile Asn Phe Cys Leu Ile Leu Ile Cys
 1               5                  10                  15

Leu Leu Leu Ile Cys Ile Ile Val Met Leu Leu
            20                  25
```

<210> SEQ ID NO 8
<211> LENGTH: 9
<212> TYPE: PRT
<213> ORGANISM: papillomavirus

<400> SEQUENCE: 8

```
Leu Leu Leu Gly Thr Leu Asn Ile Val
 1               5
```

<210> SEQ ID NO 9
<211> LENGTH: 9
<212> TYPE: PRT
<213> ORGANISM: papillomavirus

<400> SEQUENCE: 9

```
Leu Leu Met Gly Thr Leu Gly Ile Val
 1               5
```

<210> SEQ ID NO 10
<211> LENGTH: 9
<212> TYPE: PRT
<213> ORGANISM: papillomavirus

<400> SEQUENCE: 10

```
Thr Leu Gln Asp Ile Val Leu His Leu
 1               5
```

<210> SEQ ID NO 11
<211> LENGTH: 9
<212> TYPE: PRT
<213> ORGANISM: papillomavirus

<400> SEQUENCE: 11

```
Gly Leu His Cys Tyr Glu Gln Leu Val
 1               5
```

```
<210> SEQ ID NO 12
<211> LENGTH: 9
<212> TYPE: PRT
<213> ORGANISM: papillomavirus

<400> SEQUENCE: 12

Pro Leu Lys Gln His Phe Gln Ile Val
 1               5

<210> SEQ ID NO 13
<211> LENGTH: 115
<212> TYPE: PRT
<213> ORGANISM: Artificial Sequence
<220> FEATURE:
<223> OTHER INFORMATION: chimeric rat comp

<400> SEQUENCE: 13

Met Gly Lys Phe Thr Val Val Ala Ala Ala Leu Leu Leu Gly Ala
 1               5                  10                  15

Val Arg Ala Glu Gly Ser Ser Leu Gly Gly Asp Leu Ala Pro Gln Met
                20                  25                  30

Leu Arg Glu Leu Gln Glu Thr Asn Ala Ala Leu Gln Asp Val Arg Glu
            35                  40                  45

Leu Leu Arg Gln Gln Val Lys Glu Ile Thr Phe Leu Lys Asn Thr Val
    50                  55                  60

Met Glu Cys Asp Ala Cys Gly Met Gln Pro Ala Arg Thr Pro Gly Thr
65                  70                  75                  80

Ser Pro Gln Pro Gln Pro Lys Pro Gln Pro Gln Pro Gln Pro Gln Pro
                85                  90                  95

Lys Pro Gln Pro Lys Pro Glu Pro Glu Gly Thr Gly Ser Ser Glu Lys
            100                 105                 110

Asp Glu Leu
        115

<210> SEQ ID NO 14
<211> LENGTH: 387
<212> TYPE: DNA
<213> ORGANISM: Artificial Sequence
<220> FEATURE:
<223> OTHER INFORMATION: chimeric rat COMP-KDEL

<400> SEQUENCE: 14
aagcttacca tgggaaagtt cactgtggtg gcggcggcgt tgctgctgct gggcgcggtg      60
cgggccgagg gatccagcct gggtggagac ctagccccac agatgcttcg agaactccag     120
gagactaatg cggcgctgca agacgtgaga gagctcttgc gacagcaggt caaggagatc     180
accttcctga agaatacggt gatgaatgt gacgcttgcg gaatgcagcc cgcacgcacc     240
cccggtacta gtccgcagcc gcagccgaaa ccgcagccgc agccgcagcc gcagccgaaa     300
ccgcagccga aaccggaacc ggaaggtacc ggatcatcag aaaaagatga gttgtaggcg     360
gccgcagaat tccatatgca tctcgag                                         387

<210> SEQ ID NO 15
<211> LENGTH: 115
<212> TYPE: PRT
<213> ORGANISM: Artificial Sequence
<220> FEATURE:
<223> OTHER INFORMATION: chimeric rat COMP-KDEL
```

<400> SEQUENCE: 15

Met Gly Lys Phe Thr Val Val Ala Ala Ala Leu Leu Leu Leu Gly Ala
1               5                   10                  15

Val Arg Ala Glu Gly Ser Ser Leu Gly Gly Asp Cys Cys Pro Gln Met
            20                  25                  30

Leu Arg Glu Leu Gln Glu Thr Asn Ala Ala Leu Gln Asp Val Arg Glu
        35                  40                  45

Leu Leu Arg Gln Gln Val Lys Glu Ile Thr Phe Leu Lys Asn Thr Val
    50                  55                  60

Met Glu Cys Asp Ala Cys Gly Met Gln Pro Ala Arg Thr Pro Gly Thr
65                  70                  75                  80

Ser Pro Gln Pro Gln Pro Lys Pro Gln Pro Gln Pro Gln Pro Gln Pro
                85                  90                  95

Lys Pro Gln Pro Lys Pro Glu Pro Glu Gly Thr Gly Ser Ser Glu Lys
                100                 105                 110

Asp Glu Leu
        115

<210> SEQ ID NO 16
<211> LENGTH: 387
<212> TYPE: DNA
<213> ORGANISM: Artificial Sequence
<220> FEATURE:
<223> OTHER INFORMATION: chimeric rat COMP-KDEL

<400> SEQUENCE: 16
aagcttacca tgggaaagtt cactgtggtg gcggcggcgt tgctgctgct gggcgcggtg     60
cgggccgagg gatccagcct gggtggagac tgttgtccac agatgcttcg agaactccag    120
gagactaatg cggcgctgca agacgtgaga gagctcttgc gacagcaggt caaggagatc    180
accttcctga gaatacggt gatggaatgt gacgcttgcg gaatgcagcc cgcacgcacc    240
cccggtacta gtccgcagcc gcagccgaaa ccgcagccgc agccgcagcc gcagccgaaa    300
ccgcagccga aaccggaacc ggaaggtacc ggatcatcag aaaaagatga gttgtaggcg    360
gccgcagaat tccatatgca tctcgag                                        387

<210> SEQ ID NO 17
<211> LENGTH: 105
<212> TYPE: PRT
<213> ORGANISM: Artificial Sequence
<220> FEATURE:
<223> OTHER INFORMATION: chimeric mouse TSP3-KDEL

<400> SEQUENCE: 17

Met Gly Lys Phe Thr Val Val Ala Ala Ala Leu Leu Leu Leu Gly Ala
1               5                   10                  15

Val Arg Ala Glu Gly Ser Ser Leu Gly Gly Asp Cys Cys Lys Ala Leu
            20                  25                  30

Val Thr Gln Leu Thr Leu Phe Asn Gln Ile Leu Val Glu Leu Arg Asp
        35                  40                  45

Asp Ile Arg Asp Gln Val Lys Glu Met Ser Leu Ile Arg Asn Thr Ile
    50                  55                  60

Met Glu Cys Gln Val Cys Gly Pro Gln Pro Gln Pro Lys Pro Gln Pro
65                  70                  75                  80

```
Gln Pro Gln Pro Gln Pro Lys Pro Gln Pro Lys Pro Glu Pro Glu Gly
                85                  90                  95

Thr Gly Ser Ser Glu Lys Asp Glu Leu
            100                 105

<210> SEQ ID NO 18
<211> LENGTH: 357
<212> TYPE: DNA
<213> ORGANISM: Artificial Sequence
<220> FEATURE:
<223> OTHER INFORMATION: chimeric mouse TSP3-KDEL

<400> SEQUENCE: 18
aagcttacca tgggaaagtt cactgtggtg gcggcggcgt tgctgctgct gggcgcggtg      60
cgggccgagg gatccagcct gggtggagac tgttgtaagg cattggtcac ccagctcacc     120
ctcttcaacc agatcctagt ggagcttcgg gacgacatcc agaccaggt gaaggaaatg      180 tcactcatcc ggaacaccat catggagtgt caggtgtgcg gtccgcagcc gcagccgaaa     240
ccgcagccgc agccgcagcc gcagccgaaa ccgcagccga accggaacc ggaaggtacc      300 ggatcatcag aaaaagatga gttgtaggcg gccgcagaat tccatatgca tctcgag       357

<210> SEQ ID NO 19
<211> LENGTH: 109
<212> TYPE: PRT
<213> ORGANISM: Artificial Sequence
<220> FEATURE:
<223> OTHER INFORMATION: chimeric mouse TSP3-KDEL

<400> SEQUENCE: 19

Met Gly Lys Phe Thr Val Val Ala Ala Ala Leu Leu Leu Leu Gly Ala
  1               5                  10                  15

Val Arg Ala Glu Gly Ser Ser Leu Gly Gly Asp Cys Cys Gly Glu Gln
                20                  25                  30

Thr Lys Ala Leu Val Thr Gln Leu Thr Leu Phe Asn Gln Ile Leu Val
            35                  40                  45

Glu Leu Arg Asp Asp Ile Arg Asp Gln Val Lys Glu Met Ser Leu Ile
    50                  55                  60

Arg Asn Thr Ile Met Glu Cys Gln Val Cys Gly Pro Gln Pro Gln Pro
 65                  70                  75                  80

Lys Pro Gln Pro Gln Pro Gln Pro Gln Pro Lys Pro Gln Pro Lys Pro
                85                  90                  95

Glu Pro Glu Gly Thr Gly Ser Ser Glu Lys Asp Glu Leu
            100                 105

<210> SEQ ID NO 20
<211> LENGTH: 369
<212> TYPE: DNA
<213> ORGANISM: Artificial Sequence
<220> FEATURE:
<223> OTHER INFORMATION: chimeric mouse TSP3-KDEL

<400> SEQUENCE: 20
aagcttacca tgggaaagtt cactgtggtg gcggcggcgt tgctgctgct gggcgcggtg      60
cgggccgagg gatccagcct gggtggagac tgttgtgggg agcagaccaa ggcattggtc     120
acccagctca ccctcttcaa ccagatccta gtggagcttc ggacgacat ccgagaccag      180 gtgaaggaaa tgtcactcat ccggaacacc atcatggagt gtcaggtgtg cggtccgcag     240
ccgcagccga accgcagcc gcagccgcag ccgcagccga accgcagcc gaaaccggaa       300
```
ccggaaggta ccggatcatc agaaaaagat gagttgtagg cggccgcaga attccatatg    360
catctcgag                                                           369

<210> SEQ ID NO 21
<211> LENGTH: 109
<212> TYPE: PRT
<213> ORGANISM: Artificial Sequence
<220> FEATURE:
<223> OTHER INFORMATION: chimeric Xenopus laevis TSP4-KDEL

<400> SEQUENCE: 21

Met Gly Lys Phe Thr Val Val Ala Ala Leu Leu Leu Gly Ala
1               5                   10                  15

Val Arg Ala Glu Gly Ser Ser Leu Gly Gly Asp Cys Cys Gly Asp Val
            20                  25                  30

Ser Arg Gln Leu Ile Gly Gln Ile Thr Gln Met Asn Gln Met Leu Gly
        35                  40                  45

Glu Leu Arg Asp Val Met Arg Gln Gln Val Lys Glu Thr Met Phe Leu
    50                  55                  60

Arg Asn Thr Ile Ala Glu Cys Gln Ala Cys Gly Pro Gln Pro Gln Pro
65                  70                  75                  80

Lys Pro Gln Pro Gln Pro Gln Pro Gln Pro Lys Pro Gln Pro Lys Pro
                85                  90                  95

Glu Pro Glu Gly Thr Gly Ser Ser Glu Lys Asp Glu Leu
            100                 105

<210> SEQ ID NO 22
<211> LENGTH: 369
<212> TYPE: DNA
<213> ORGANISM: Artificial Sequence
<220> FEATURE:
<223> OTHER INFORMATION: chimeric Xenopus laevis TSP4-KDEL

<400> SEQUENCE: 22
aagcttacca tgggaaagtt cactgtggtg gcggcggcgt tgctgctgct gggcgcggtg    60
cgggccgagg gatccagcct gggtggagac tgttgtggtg acgtcagcag acagttgatt    120
ggccagataa cccaaatgaa tcagatgctg ggagagctcc gagatgtcat gagacagcag    180
gtgaaagaga ccatgttctt gagaaacacc attgcagaat gccaggcctg tggcccgcag    240
ccgcagccga accgcagcc gcagccgcag ccgcagccga accgcagcc gaaaccggaa    300 ccggaaggta ccggatcatc agaaaaagat gagttgtagg cggccgcaga attccatatg    360
catctcgag                                                           369

<210> SEQ ID NO 23
<211> LENGTH: 109
<212> TYPE: PRT
<213> ORGANISM: Artificial Sequence
<220> FEATURE:
<223> OTHER INFORMATION: chimeric human COMP-KDEL

<400> SEQUENCE: 23

Met Arg Tyr Met Ile Leu Gly Leu Leu Ala Leu Ala Ala Val Cys Ser
1               5                   10                  15

Ala Ala Lys Lys Gly Ser Ser Leu Gly Gly Asp Cys Cys Ser Asp Leu
            20                  25                  30

Gly Pro Gln Met Leu Arg Glu Leu Gln Glu Thr Asn Ala Ala Leu Gln
        35                  40                  45

```
Asp Val Arg Asp Trp Leu Arg Gln Gln Val Arg Glu Ile Thr Phe Leu
        50                  55                  60

Lys Asn Thr Val Met Glu Cys Asp Ala Cys Gly Pro Gln Pro Gln Pro
 65                  70                  75                  80

Lys Pro Gln Pro Gln Pro Gln Pro Lys Pro Gln Pro Lys Pro
                85                  90                  95

Glu Pro Glu Gly Thr Gly Ser Ser Glu Lys Asp Glu Leu
            100                 105

<210> SEQ ID NO 24
<211> LENGTH: 372
<212> TYPE: DNA
<213> ORGANISM: Artificial Sequence
<220> FEATURE:
<223> OTHER INFORMATION: chimeric human COMP-KDEL

<400> SEQUENCE: 24
aagcttacca tgggaaggta catgatttta ggcttgctcg cccttgcggc agtctgcagc    60
gctgccaaaa aaggatccag cctgggtgga gactgttgtt cagacctggg cccgcagatg   120
cttcgggaac tgcaggaaac caacgcggcg ctgcaggacg tgcgggactg gctgcggcag   180
caggtcaggg agatcacgtt cctgaaaaac acggtgatgg agtgtgacgc gtgcgggccg   240
cagccgcagc cgaaaccgca gccgcagccg cagccgcagc cgaaaccgca gccgaaaccg   300
gaaccggaag gtaccggatc atcagaaaaa gatgagttgt aggcggccgc agaattccat   360
atgcatctcg ag                                                      372

<210> SEQ ID NO 25
<211> LENGTH: 90
<212> TYPE: PRT
<213> ORGANISM: Artificial Sequence
<220> FEATURE:
<223> OTHER INFORMATION: chimeric human PLB-KDEL

<400> SEQUENCE: 25

Met Arg Tyr Met Ile Leu Gly Leu Leu Ala Leu Ala Ala Val Cys Ser
  1               5                  10                  15

Ala Ala Lys Lys Gly Ser Ser Leu Gly Gly Asp Cys Cys Gln Lys Leu
                20                  25                  30

Gln Asn Leu Phe Ile Asn Phe Cys Leu Ile Leu Ile Cys Leu Leu Leu
            35                  40                  45

Ile Cys Ile Ile Val Met Leu Leu Pro Gln Pro Gln Pro Lys Pro Gln
 50                  55                  60

Pro Gln Pro Gln Pro Gln Pro Lys Pro Gln Pro Lys Pro Glu Pro Glu
 65                  70                  75                  80

Gly Thr Gly Ser Ser Glu Lys Asp Glu Leu
            85                  90

<210> SEQ ID NO 26
<211> LENGTH: 315
<212> TYPE: DNA
<213> ORGANISM: Artificial Sequence
<220> FEATURE:
<223> OTHER INFORMATION: chimeric human PLB-KDEL

<400> SEQUENCE: 26
aagcttacca tgggaaggta catgatttta ggcttgctcg cccttgcggc agtctgcagc    60
gctgccaaaa aaggatccag cctgggtgga gactgttgtc aaaagctaca gaatctattt   120
atcaatttct gtctcatctt aatatgtctc ttgctgatct gtatcatcgt gatgcttctc   180
```

```
ccgcagccgc agccgaaacc gcagccgcag ccgcagccgc agccgaaacc gcagccgaaa      240
ccggaaccgg aagtaccgga tcatcagaaa aagatgagtt gtaggcggc cgcagaattc      300 catatgcatc tcgag                                                      315
```

<210> SEQ ID NO 27
<211> LENGTH: 109
<212> TYPE: PRT
<213> ORGANISM: Artificial Sequence
<220> FEATURE:
<223> OTHER INFORMATION: chimeric human TSP3-KDEL

<400> SEQUENCE: 27

```
Met Arg Tyr Met Ile Leu Gly Leu Leu Ala Leu Ala Ala Val Cys Ser
 1               5                  10                  15

Ala Ala Lys Lys Gly Ser Ser Leu Gly Gly Asp Cys Cys Gly Glu Gln
            20                  25                  30

Thr Lys Ala Leu Val Thr Gln Leu Thr Leu Phe Asn Gln Ile Leu Val
        35                  40                  45

Glu Leu Arg Asp Asp Ile Arg Asp Gln Val Lys Glu Met Ser Leu Ile
    50                  55                  60

Arg Asn Thr Ile Met Glu Cys Gln Val Cys Gly Pro Gln Pro Gln Pro
65                  70                  75                  80

Lys Pro Gln Pro Gln Pro Gln Pro Lys Pro Gln Pro Lys Pro
                85                  90                  95

Glu Pro Glu Gly Thr Gly Ser Ser Glu Lys Asp Glu Leu
            100                 105
```

<210> SEQ ID NO 28
<211> LENGTH: 372
<212> TYPE: DNA
<213> ORGANISM: Artificial Sequence
<220> FEATURE:
<223> OTHER INFORMATION: chimeric human TSP3-KDEL

<400> SEQUENCE: 28

```
aagcttacca tgggaaggta catgatttta ggcttgctcg cccttgcggc agtctgcagc      60
gctgccaaaa aaggatccag cctgggtgga gactgttgtg gggagcagac caaggcattg     120
gtcacccagc tcaccctctt caaccagatc ctagtggagc ttcgggacga catccgagac     180
caggtgaagg aaatgtcact catccggaac accatcatgg agtgtcaggt gtgcggtccg     240
cagccgcagc cgaaaccgca gccgcagccg cagccgcagc cgaaaccgca gccgaaaccg     300
gaaccggaag gtaccggatc atcagaaaaa gatgagttgt aggcggccgc agaattccat     360
atgcatctcg ag                                                          372
```

<210> SEQ ID NO 29
<211> LENGTH: 109
<212> TYPE: PRT
<213> ORGANISM: Artificial Sequence
<220> FEATURE:
<223> OTHER INFORMATION: chimeric human TSP4-KDEL

<400> SEQUENCE: 29

```
Met Arg Tyr Met Ile Leu Gly Leu Leu Ala Leu Ala Ala Val Cys Ser
 1               5                  10                  15

Ala Ala Lys Lys Gly Ser Ser Leu Gly Gly Asp Cys Cys Gly Asp Phe
            20                  25                  30

Asn Arg Gln Phe Leu Gly Gln Met Thr Gln Leu Asn Gln Leu Leu Gly
        35                  40                  45
```

```
Glu Val Lys Asp Leu Leu Arg Gln Gln Val Lys Glu Thr Ser Phe Leu
         50                  55                  60

Arg Asn Thr Ile Ala Glu Cys Gln Ala Cys Gly Pro Gln Pro Gln Pro
 65                  70                  75                  80

Lys Pro Gln Pro Gln Pro Gln Pro Lys Pro Gln Pro Lys Pro
                 85                  90                  95

Glu Pro Glu Gly Thr Gly Ser Ser Glu Lys Asp Glu Leu
                100                 105
```

<210> SEQ ID NO 30
<211> LENGTH: 372
<212> TYPE: DNA
<213> ORGANISM: Artificial Sequence
<220> FEATURE:
<223> OTHER INFORMATION: chimeric human TSP4-KDEL

<400> SEQUENCE: 30

```
aagcttacca tgggaaggta catgatttta ggcttgctcg cccttgcggc agtctgcagc      60
gctgccaaaa aaggatccag cctggtggga gactgttgtg gggactttaa ccggcagttc     120
ttgggtcaaa tgacacaatt aaaccaactc ctgggagagg tgaaggacct tctgagacag     180
caggttaagg aaacatcatt tttgcgaaac accatagctg aatgccaggc ttgcggtccg     240
cagccgcagc cgaaaccgca gccgcagccg cagccgcagc cgaaaccgca gccgaaaccg     300
gaaccggaag gtaccggatc atcagaaaaa gatgagttgt aggcggccgc agaattccat     360
atgcatctcg ag                                                        372
```

<210> SEQ ID NO 31
<211> LENGTH: 8
<212> TYPE: PRT
<213> ORGANISM: Artificial Sequence
<220> FEATURE:
<223> OTHER INFORMATION: peptide that binds to erd2 receptor

<400> SEQUENCE: 31

```
Tyr Thr Ser Glu Lys Asp Glu Leu
 1               5
```

<210> SEQ ID NO 32
<211> LENGTH: 8
<212> TYPE: PRT
<213> ORGANISM: Artificial Sequence
<220> FEATURE:
<223> OTHER INFORMATION: peptide that binds to erd2 receptor

<400> SEQUENCE: 32

```
Leu Asn Tyr Phe Asp Asp Glu Leu
 1               5
```

<210> SEQ ID NO 33
<211> LENGTH: 9
<212> TYPE: PRT
<213> ORGANISM: Artificial Sequence
<220> FEATURE:
<223> OTHER INFORMATION: alpha-five integrin binding motif

<400> SEQUENCE: 33

```
Cys Asp Cys Arg Gly Asp Cys Phe Cys
 1               5
```

<210> SEQ ID NO 34
<211> LENGTH: 134
<212> TYPE: PRT

<210> SEQ ID NO 34 (implied continuation)
<213> ORGANISM: Artificial Sequence
<220> FEATURE:
<223> OTHER INFORMATION: KDEL/myc

<400> SEQUENCE: 34

```
Met Gly Lys Phe Thr Val Val Ala Ala Leu Leu Leu Gly Ala
 1               5                  10                  15

Val Arg Ala Glu Gly Ser Glu Gln Lys Leu Ile Ser Glu Glu Asp Leu
            20                  25                  30

Tyr His Pro Asn Ser Thr Cys Gly Ser Ser Leu Gly Gly Asp Cys Cys
            35                  40                  45

Pro Gln Met Leu Arg Glu Leu Gln Glu Thr Asn Ala Ala Leu Gln Asp
        50                  55                  60

Val Arg Glu Leu Leu Arg Gln Gln Val Lys Glu Ile Thr Phe Leu Lys
 65                 70                  75                  80

Asn Thr Val Met Glu Cys Asp Ala Cys Gly Met Gln Pro Ala Arg Thr
                85                  90                  95

Pro Gly Thr Ser Pro Gln Pro Gly Pro Lys Pro Gln Pro Gln Pro Gln
            100                 105                 110

Pro Gln Pro Lys Pro Gln Pro Lys Pro Glu Pro Glu Gly Thr Gly Ser
        115                 120                 125

Ser Glu Lys Asp Glu Leu
    130
```

<210> SEQ ID NO 35
<211> LENGTH: 444
<212> TYPE: DNA
<213> ORGANISM: Artificial Sequence
<220> FEATURE:
<223> OTHER INFORMATION: KDEL-myc

<400> SEQUENCE: 35

```
aagcttacca tgggaaagtt cactgtggtg gcggcggcgt tgctgctgct gggcgcggtg      60
cgggccgagg gatccgaaca aaaacttatt tctgaagaag acttgtacca cccaaactca     120
acatgcggat ccagcctggg tggagactgt tgtccacaga tgcttcgaga actccaggag     180
actaatgcgg cgctgcaaga cgtgagagag ctcttgcgac agcaggtcaa ggagatcacc     240
ttcctgaaga atacggtgat ggaatgtgac gcttgcggaa tgcagcccgc acgcaccccc     300
ggtactagtc cgcagccgca gccgaaaccg cagccgcagc cgcagccgca gccgaaaccg     360
cagccgaaac cggaaccgga aggtaccgga tcatcagaaa aagatgagtt gtaggcggcc     420
gcagaattcc atatgcatct cgag                                            444
```

<210> SEQ ID NO 36
<211> LENGTH: 10
<212> TYPE: PRT
<213> ORGANISM: Artificial Sequence
<220> FEATURE:
<223> OTHER INFORMATION: human myc tag

<400> SEQUENCE: 36

```
Glu Gln Lys Leu Ile Ser Glu Glu Asp Leu
 1               5                  10
```

```
<210> SEQ ID NO 37
<211> LENGTH: 4
<212> TYPE: PRT
<213> ORGANISM: Artificial Sequence
<220> FEATURE:
<223> OTHER INFORMATION: recognition sequence of KDEL receptor

<400> SEQUENCE: 37

Lys Asp Glu Leu
 1

<210> SEQ ID NO 38
<211> LENGTH: 4
<212> TYPE: PRT
<213> ORGANISM: Artificial Sequence
<220> FEATURE:
<223> OTHER INFORMATION: binds to KDEL receptor
<223> OTHER INFORMATION: Xaa= any amino acid

<400> SEQUENCE: 38

Xaa Asp Glu Leu
 1

<210> SEQ ID NO 39
<211> LENGTH: 6
<212> TYPE: PRT
<213> ORGANISM: Artificial Sequence
<220> FEATURE:
<223> OTHER INFORMATION: binds to KDEL receptor

<400> SEQUENCE: 39

Ser Glu Lys Asp Glu Leu
 1               5

<210> SEQ ID NO 40
<211> LENGTH: 4
<212> TYPE: PRT
<213> ORGANISM: Ratus ratus

<400> SEQUENCE: 40

Gly Asp Leu Ala
 1

<210> SEQ ID NO 41
<211> LENGTH: 4
<212> TYPE: PRT
<213> ORGANISM: Ratus ratus
<220> FEATURE:
<221> NAME/KEY: VARIANT
<222> LOCATION: (0)...(0)

<400> SEQUENCE: 41

Gly Asp Cys Cys
 1

<210> SEQ ID NO 42
<211> LENGTH: 4
<212> TYPE: PRT
<213> ORGANISM: Mus musculus

<400> SEQUENCE: 42

Gly Glu Gln Thr
```